(12) United States Patent
Hirschhorn et al.

(10) Patent No.: US 7,829,281 B2
(45) Date of Patent: Nov. 9, 2010

(54) COMPOSITIONS AND METHODS FOR OBESITY SCREENING USING POLYMORPHISMS IN NPY2R

(75) Inventors: Joel Hirschhorn, Newtown Center, MA (US); Catarina deHaseth Campbell, Brookline, MA (US); Kristin Ardlie, Boston, MA (US)

(73) Assignees: Children's Medical Center Corporation, Boston, MA (US); Seracare Life Sciences, Inc., West Bridgewater, MA (US)

( * ) Notice: Subject to any disclaimer, the term of this patent is extended or adjusted under 35 U.S.C. 154(b) by 108 days.

(21) Appl. No.: 11/663,052

(22) PCT Filed: Sep. 19, 2005

(86) PCT No.: PCT/US2005/033468

§ 371 (c)(1),
(2), (4) Date: Dec. 4, 2007

(87) PCT Pub. No.: WO2006/034188

PCT Pub. Date: Mar. 30, 2006

(65) Prior Publication Data

US 2008/0102456 A1  May 1, 2008

Related U.S. Application Data

(60) Provisional application No. 60/610,992, filed on Sep. 17, 2004.

(51) Int. Cl.
*C07H 21/04* (2006.01)
*C12Q 1/68* (2006.01)

(52) U.S. Cl. .......................... 435/6; 435/91.1; 435/91.2; 536/23.1; 536/24.3

(58) Field of Classification Search ...................... None
See application file for complete search history.

(56) References Cited

U.S. PATENT DOCUMENTS

2003/0092019 A1 * 5/2003 Meyer et al. .................... 435/6

FOREIGN PATENT DOCUMENTS

WO         03/097683         11/2003

OTHER PUBLICATIONS

Hung et al. (Diabètes, vol. 53, pp. 2461-2466, Sep. 2004).*
Ma et al. (Diabetes, vol. 54, pp. 1598-1602, May 2005).*
Torekov et al. (Diebetologia, vol. 49, pp. 2653-2658, 2006).*
Siddiq (Diabetologia et al., vol. 50, pp. 574-584, 2007).*
Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Engert et al., "5' Flanking Variants Of Resistin Are Associated With Obesity", *Diabetes*, vol. 51, pp. 1629-1634, 2002.
Hirschhorn et al., "Editorial: Once and Again—Issues Surrounding Replication In Genetic Association Studies", *The Journal of Clinical Endocrinology & Metabolism*, vol. 87, pp. 4438-4441, 2002.
Lohmueller et al., "Meta-Analysis Of Genetic Association Studies Supports A Contribution Of Common Variants To Susceptibility to Common Disease", *Nature Genetics*, vol. 33, pp. 177-182, 2003.
Matsumoto et al., "Inactivation of a Novel Neuropeptide Y/Peptide YY Receptor Gene In Primate Species", *The Journal of Biological Chemistry*, vol. 271, pp. 27217-27220, 1996.
Michel et al., "XVI. International Union Of Pharmacology Recommendations For The Nomenclature Of Neuropeptide Y, Peptide YY, And Pancreatic Polypeptide Receptors", *Pharmacological Reviews*, vol. 50, pp. 143-150, 1998.
Wraith et al., "Evolution Of The Neuropeptide Y Receptor Family: Gene And Chromosome Duplications Deduced From The Cloning And Mapping Of The Five Receptor Subtype Genes In Pig", *Genome Research*, vol. 10, pp. 302-310, 2000.
Ma et al., "Variations In Peptide YY and Y2 Receptor Genes Are Associated With Severe Obesity In Pima Indian Men", Diabetes, vol. 54, pp. 1598-1602, 2005.
Database SNP DB (Online); NCBI: Oct. 10, 2003; rs2880416, XP002515186.
Database SP DB (Online); NCBI: Apr. 3, 2004; rs12507396; XP002515187.
Campbell et al., "Genetic Variation Upstream of NPY2R Is Associated With Obesity In Men", Retrieved from the Internet, URL:http://www.ashg.org/genetics/abstracts/abs04/f2251.htm; XP002515185; Oct. 30, 2004.
Campbell et al., Diabetes, vol. 56, No. 5, pp. 1460-1467, May 2007.
Database SNP DB [Online] NCBI; Oct. 10, 2003, "rs2342676" retrieved from www.NCBI.NLM.NIH.GOV Database accession No. rs2342676.
Database SNP DB [Online] NCBI; Apr. 3, 2004, "rs12649641" retrieved from www.NCBI.NLM.NIH.GOV Database accession No. rs12649641.

(Continued)

*Primary Examiner*—Jeanine A Goldberg
(74) *Attorney, Agent, or Firm*—Thomas J. Engellenner; Nutter McClennen & Fish LLP

(57) ABSTRACT

Methods and constructs are provided that are predictive of a subject's susceptibility to developing a metabolic disorder, such as obesity. The disclosed naturally-occurring SNPs located upstream of the NPY2R gene can be used as targets for the design of diagnostic reagents and the development of therapeutic agents, as well as for disease association and linkage analysis. In particular, the SNPs of the present invention are useful for identifying an individual who is at an increased or decreased risk of developing metabolic disorders, such as obesity and diabetes, and for early detection of the disease, for providing clinically important information for the prevention and/or treatment of metabolic disorder, and for screening and selecting therapeutic agents. The SNPs disclosed herein are also useful for human identification applications. Methods, assays, kits, and reagents for detecting the presence of these polymorphisms and their encoded products are provided.

9 Claims, 13 Drawing Sheets

OTHER PUBLICATIONS

Database SNP DB [Online] NCBI; Apr. 3, 2004, "rs11099992" retrieved from www.NCBI.NLM.NIH.GOV Database accession No. rs11099992.

Database SNP DB [Online] NCBI; Oct. 10, 2003, "rs6857530" retrieved from www.NCBI.NLM.NIH.GOv Database accession No. rs6857530.

* cited by examiner

FIGURE 4

Summary of Results

|  | # of SNPs | Average Spacing | # of htSNPs | Blocks | US Cauc. SNP or Hap. assoc (p<.05) | Replicated in Poland |
|---|---|---|---|---|---|---|
| NPY | 21 | 1.7 kb | 8 | 1 | No | No sig. SNPs/Haps. |
| PPY and PYY | 26 | 1.7 kb | 13 | 3 | Yes | No |
| NPY1R and 5R | 45 | 2.5 kb | 22 | 5 | No | No Sig. SNPs/Haps. |
| NPY2R | 31 | 1.6 kb | 13 | 3 | Yes | Yes |

FIGURE 6

NPY2R SNPs associated with obesity in men

|  | P-Value | | Odds ratio | |
|---|---|---|---|---|
|  | USWT | POLWT | USWT | POLWT |
| rs2342676 | 0.050 | 0.079 | 0.801 | 0.771 |
| hCV44828 | 0.016 | 0.138 | 1.297 | 1.241 |
| hCV44829 | 0.036 | 0.097 | 0.782 | 0.775 |
| hCV1526995 | 0.015 | 0.057 | 1.344 | 1.337 |
| hCV44837 | 0.006 | 0.091 | 0.728 | 0.783 |

FIGURE 9

Haplotype Analysis: NPY2R

Men: Block 2

| | Haplotype | Frequency | | P-value | | Odds Ratio | |
|---|---|---|---|---|---|---|---|
| | | US | POL | US | POL | US | POL |
| 1 | hGACAGAA | 0.40 | 0.35 | 0.098 | 0.659 | 0.841 | 0.939 |
| 2 | hGGAGAAG | 0.26 | 0.32 | 0.013 | 0.042 | 1.344 | 1.362 |
| 3 | hCACAGTA | 0.10 | 0.15 | 0.180 | 0.293 | 0.803 | 0.809 |
| 4 | hGGAAGAG | 0.08 | 0.06 | 0.804 | 0.609 | 0.952 | 0.858 |

Pooled OR=1.35
95% CI=1.12–1.62
P-value=0.0014

```
2 - GGAAGCCTGAAG
1 - GAGCAGTAAGAA
4 - GGAAACCTAGAG
  - CAGCAGTAAGAA
3 - CAGCAGTAAGTA
  - GAGAAGCCTAGAA
  - GGAAGCCTGAAA
  - GGAAGCCTAGAG
```

FIGURE 10

NPY2R in Waist-Hip Ratio Trios

- TDTs for male offspring above and below median BMI

- Fathers used as case-control study: cases above median BMI, controls below median BMI

| | US and POL | | WHR trios | | |
|---|---|---|---|---|---|
| | P-value | OR | One Tailed P-value | Pooled WHR OR | 95% CI |
| rs2342676 | 0.0087 | 0.790 | 0.0735 | 0.864 | |
| hCV44828 | 0.0048 | 1.277 | 0.0704 | 1.156 | |
| hCV44829 | 0.0076 | 0.779 | 0.1127 | 0.883 | |
| hCV1526995 | 0.0019 | 1.341 | 0.0468 | 1.185 | |
| hCV44837 | 0.0013 | 0.749 | 0.0343 | 0.835 | |

FIGURE 11

European derived Populations: Combined Values

USWT, POLWT, and WHR trios:

| | P-value | Pooled OR | 95% CI |
|---|---|---|---|
| rs2342676 | 3.43×10⁻³ | 0.822 | 0.721-0.937 |
| hCV44828 | 1.97×10⁻³ | 1.223 | 1.077-1.389 |
| hCV44829 | 5.14×10⁻³ | 0.825 | 0.722-0.942 |
| hCV1526995 | 6.34×10⁻⁴ | 1.267 | 1.106-1.451 |
| hCV44837 | 3.11×10⁻⁴ | 0.786 | 0.690-0.895 |

FIGURE 12

NPY2R in African American Weight Panel

MEN - Significant SNPs from US and Poland

| | P-Value | | | Odds ratio | | |
|---|---|---|---|---|---|---|
| | USWT | POLWT | AAWT | USWT | POLWT | AAWT |
| rs2342676 | 0.050 | 0.790 | 0.811 | 0.801 | 0.771 | 1.053 |
| hCV44828 | 0.016 | 0.138 | 0.745 | 1.297 | 1.241 | 0.934 |
| hCV44829 | 0.036 | 0.097 | 0.195 | 0.782 | 0.775 | 0.702 |
| hCV1526995 | 0.015 | 0.057 | 0.893 | 1.344 | 1.337 | 0.955 |
| hCV44837 | 0.005 | 0.091 | 0.702 | 0.728 | 0.783 | 1.092 |

One SNP trends in the same direction
P-values in AAWT are not significant
Odds ratios not always same direction

SEQUENCE LISTING

```
<160> NUMBER OF SEQ ID NOS: 8

<210> SEQ ID NO 1
<211> LENGTH: 511
<212> TYPE: DNA
<213> ORGANISM: Homo sapiens
<220> FEATURE:
<221> NAME/KEY: misc_feature
<222> LOCATION: (256)..(256)
<223> OTHER INFORMATION: n = a or g

<400> SEQUENCE: 1
aaactgattg tcttgcttta tttaaatgct tgatacgttt agtgaatatt tttaagctta      60
ttaagtccct cttgtagaac tagtatttaa agtttcaata attgccttgt agcaaaaatt     120
atggaaccta gatatcctaa tggccatttg gttataatat agattctcaa taggtcatat     180
ggatatttct gtttggatct atgcctgctt ttcctttcat ggaggagaag gagcagaagg     240
agttaatacc tgaacngata taattggggc tgcatcaaat acacatataa aaaagtctat     300
ataagtgtac tactttaaaa tagtcttttt aaaaaaaact tcacttttg aaaaactagt      360 caatctaatc aagtttgttc tgatgaaaaa ttgacttcct tctctgacct tcatttgtag     420
cgagtagtcc agtaaagttt gaatgggcaa gaaatggtca tcaaatcgtg aacttcacaa     480
atctcatagg ctaaattttct taaaatattt g                                   511

<210> SEQ ID NO 2
<211> LENGTH: 601
<212> TYPE: DNA
<213> ORGANISM: Homo sapiens
```

```
<220> FEATURE:
<221> NAME/KEY: misc_feature
<222> LOCATION: (301)..(301)
<223> OTHER INFORMATION: n = a or c

<400> SEQUENCE: 2
gtctttgttt gtttaaccta agaagttaag tacatgactt tattagcttc tctgagcttt    60
tcttacatta ctggagttaa gataattctt ccacttcagc tggctgtgct cacttttgg    120 tcctgtgctc ttcctcsctt cctcaaattt cttccttttg gccagtggcc tgatttgtgg    180
gtttacttct tttctttggg aatcagcttc cacattccag cggaactgca ccactttgtt    240
ctgtctgtgg cttaagtcag gttgatatgg cttacaagtt actcaataat ctctcaggga    300
ncgctgatat taaggtgagg ggaaaaaaaa aaaaacgaaa aagctagctt tctggcagag    360
tgaaaacagg aaaccctgga atccaagaa acttattctc ttgtgctttt ttttcctcct    420
gatttagttt ccccacttca atcttcccca cctggggcca ctgaaatttt atactgaaca    480
ctttacgtgg actccatgtt acctgaagta tttgcctttt catggaagaa gtttcttggt    540
tttcccatca ttcaatttaa cctttgtggt taaggtttat gtaatgtgaa cttggcttaa    600
g                                                                    601

<210> SEQ ID NO 3
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: n = a or g

<400> SEQUENCE: 3
tgggtttact tctttctttt gggaatcagc ttccacattc cagcggaact gcaccacttt    60
gttctgtctg tggcttaagt caggttgata tggcttacaa gttactcaat aatctctcag    120
ggaccgctga tattaaggtg agggaaaaa aaaaaaaacg aaaaagctag ctttctggca    180
gagtgaaaac aggaaaccct ggaatccaaa gaaacttatt ctcttgtgct tttttttcct    240
cctgatttag tttcccccact tcaatcttcc ccacctgggg ccactgaaat tttatactga    300
ncactttacg tggactccat gttacctgaa gtatttgcct tttcatggaa gaagtttctt    360
ggttttccca tcattcaatt taaccttgt ggttaaggtt tatgtaatgt gaacttggct    420
taaggaaaaa attttaaaat acctcgctct tactccctgc tggatttatg tgaaagaaat    480
aactggacaa aggtactgca aatatatcca agatcatttc tcacagtttt gtccataaca    540
acaataactc atgagaatat aatcatacag tttatgacta ggcaaccatt aaaggaagga    600
t                                                                    601

<210> SEQ ID NO 4
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: n = a or g

<400> SEQUENCE: 4
ttctatatta actgaagatt aatttcaggt tacactgtaa aaatgcctta caaatgcaat    60
actattaggg tgtggaaaac cctgaaggaa ctgaaaatcc aatccatttg agggaagcct   120
```

-continued

```
ttaattaaca tcttggagaa tatgtattac cttttttaaac agataaatat ttttttttcat    180 tttagagtag cggaatctaa tcttaatcta atcttttagg agtatatttc agagaaattc    240
caagcacacc agtatgacca tccttatttc agaaatgaca atgcatagag gaaaagtaat    300
ntgtgcaaag cctccgaaga ggatggttaa gtaaagactt aggttaccag tatcaggctt    360 tcgttttttgt atgtaggtag ctctactgcc tcctcttaaa accaacaaag gaaagagaga    420
ctggctgcaa acttttagaa ggaatggctt cgaatagggt tcctgggagg aatcccgagg    480
aaatagacgc tgctgctctg ctgattgtct ccactatcct gttttgctcc tacccactaa    540
tccagcctgg gaggctctgg gcattagcgg aaggcttcac cacaaggaga caggagcgag    600
t                                                                     601
```

<210> SEQ ID NO 5
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: n = a or g

<400> SEQUENCE: 5

```
agcggaaggc ttcaccacaa ggagacagga gcgagtattc cataggcatg cgctcctagt     60
ggcacgagtg gcttgggtca ggatcaaaga gtgaaggatt cggaagtcag ctatctggag    120
agagagagag agagattgtg ttttattcgt gtcccatagc tttcctatcc tatccctatc    180
ctagctttta acctgagcca gagctcacta cacaggttcc tggctatcga gtctgaatct    240
gcactactca acttataaac tgtctgcaga cacctgttag ggaaattgct gatcatgggc    300
ngcaggatct gaactcgctt taccttctcg tttggagcac agggaccgcc cagctagagg    360
agcaccagcg cactgcgccc cagccctggg cgagggtgcg gaggatttgt tctcggtgca    420
atcctgctgg cgcttttccg gggttctgcg cggatccagc tccccatctc tgctcctaca    480
cacacaaaag aaaacaactc tcgattggaa gttgtggaat tttctcagcc cctacgaggc    540
gcggggattc tccagccccg gccctcctcc cgccagcctg aggtctcctt cgctcgcctg    600
c                                                                     601
```

<210> SEQ ID NO 6
<211> LENGTH: 3747
<212> TYPE: DNA
<213> ORGANISM: Homo sapiens

<400> SEQUENCE: 6

```
gaattcggcc gctgagagac cctggacact gttcctgctc cctcgccacc aaaacttctc     60
ctccagtccc ctcccctgca ggaccatcgc ccgcagcctc tgcacctgtt ttcttgtgtt    120
taagggtggg gtttgccccc ctccccacgc tcccatctct gatcctccca ccttcacccg    180 cccacccccgc gagtgagtgc ggtgcccagg cgcgcttggc ctgagaggtc ggcagcagac    240
ccggcagcgc caaccgccca gccgctctga ctgctccggc tgcccgcccg cgcggcgcgg    300
gctgtcctgg accctaggag gggacggaac cggacttgcc tttgggcacc ttccagggcc    360
ctctccaggt cggctggcta atcatcggac agacggactg cacacatctt gtttccgcgt    420
ctccgcaaaa acgcgaggtc caggtcagtt gtagactctt gtgctggttg caggccaagt    480
ggacctgtac tgaaaatggg tccaataggt gcagaggctg atgagaacca gacagtggaa    540
gaaatgaagg tggaacaata cgggccacaa acaactccta gaggtgaact ggtccctgac    600
```

```
cctgagccag agcttataga tagtaccaag ctgattgagg tacaagttgt tctcatattg    660
gcctactgct ccatcatctt gcttggggta attggcaact ccttggtgat ccatgtggtg    720
atcaaattca agagcatgcg cacagtaacc aacttttca ttgccaatct ggctgtggca    780
gatcttttgg tgaacactct gtgtctaccg ttcactctta cctataccct aatggggag    840 tggaaaatgg gtcctgtcct gtgccacctg gtgccctatg cccagggcct ggcagtacaa    900
gtatccacaa tcaccttgac agtaattgcc ctggaccggc acaggtgcat cgtctaccac    960
ctagagagca agatctccaa gcgaatcagc ttcctgatta ttggcttggc ctggggcatc   1020
agtgccctgc tggcaagtcc cctggccatc ttccgggagt attcgctgat tgagatcatt   1080
ccggactttg agattgtggc ctgtactgaa aagtggcctg cgaggagaa gagcatctat    1140 ggcactgtct atagtctttc ttccttgttg atcttgtatg ttttgcctct gggcattata   1200 tcatttcct acactcgcat ttggagtaaa ttgaagaacc atgtcagtcc tggagctgca   1260
aatgaccact accatcagcg aaggcaaaaa accaccaaaa tgctggtgtg tgtggtggtg   1320
gtgtttgcgg tcagctggct gcctctccat gccttccagc ttgccgttga cattgacagc   1380
caggtcctgg acctgaagga gtacaaactc atcttcacag tgttccacat tatcgccatg   1440
tgctccactt ttgccaatcc ccttctctat ggctggatga acagcaacta cagaaaggct   1500
ttcctctcgg ccttccgctg tgagcagcgg ttggatgcca ttcactctga ggtgtccgtg   1560
acattcaagg ctaaaaagaa cctggaggtc agaaagaaca gtggcccaa tgactctttc   1620 acagaggcta ccaatgtcta aggaagctgt ggtgtgaaaa tgtatggatg aattctgacc   1680
agagctatga atctggttga tggcggctca caagtgaaaa ctgatttccc attttaaaga   1740
agaagtggat ctaaatggaa gcatctgctg tttaattcct ggaaaactgg ctgggcagag   1800
cctgtgtgaa atactggaa ttcaaagata aggcaacaaa atggtttact taacagttgg   1860
ttgggtagta ggttgcatta tgagtaaaag cagagagaag tacttttgat tattttcctg   1920
gagtgaagaa aacttgaaca agaaattggt attatcaaag cattgctgag agacggtggg   1980
aaaataagtt gactttcaaa tcacgttagg acctggattg aggaggtgtg cagttcgctg   2040
ctccctgctt ggcttatgaa acaccactg aacagaaatt tctccaggga gccacaggct   2100
ctccttcatc gcattttgat ttttttgttc attctctaga caaatccat cagggaatgc   2160 tgcaggaaac gattgccaac tatacgaatg gcttcgagga gataaactga aatttgctat   2220
ataattaata ttttggcaga tgataggga actcctcaac actcagtggg ccaattgttc   2280 ttaaaccaa ttgcacgttt ggtgaaagtt tcttcaactc tgaatcaaaa gctgaaattc   2340
tcagaattac aggaaatgca aaccatcatt taatttctaa tttcaagtta catccgcttt   2400
atggagatac tatttagata acaagaatac aacttgatac ttttattgtt atacctttt   2460 gaacatgtat gatttctgtt gttattccta ttggagctaa gtttgtctac actaaaattt   2520
aaatcagact agagaataat ttttgtggca tgttgtaaca tttcacagta tttacaagct   2580
atttttgcac aggtacatag ctctcatgta tttaaagaac actgcagtgt tattttcttt   2640
gaaattcatc ctccacggac ccattcatac taaataaaac aatgtaatta cattaaaatg   2700
gacctatctg taagaggtac taaaaacact ggattcattt catcttgcaa atgttgtatt   2760
tcaaaccagt ttcacataag ttatttgtct tcttttcaaa ataattagct atatttttat   2820
ataatatgaa tatatacata aaaattgttt ctataaattg tagaacatag atgctacagt   2880
attttttatt taattatatt atgaataaaa ttgttatttc aatagtaccc aaccaaagat   2940
```

```
gcttaaaaac cttctatgtt cataaaaaat aacaactgag atgttaaaat agtcatacgt      3000
ctttagatgc tattaaagtt tcattagtca tattttttgta aatatgacag aatttgtgaa      3060 tatatttta aagcaaaaaa cttcaacatg catatgatat atagttacaa cattaatttt      3120
atgaactgga gagctttact ttgtggatat atttaaaatt catattatag ctcctattaa      3180
attccttcca tgatagatat aaaggactgg ttttttaagtg cactgcactt ctggaatact      3240
gaaaaagaat gaaaacaata tgttagatta ggtgtaagac tttaagaagc gaacaaaaag      3300
taatgtatat ctgtaatata taatcaaatg attcattttt ctgttagact aggcaaattg      3360
ttcaaaaata accttttttgt cttttaagta gcagtcactt tgcttaagat gctaatagaa      3420
aactgtggtt aaagatttac cctccctctt ggtgaattat tacactgtaa gaaatgtata      3480
tgctactgtg ttacatgttg tattagtaaa ttattagaat ccaattaatg attcaattaa      3540
catatatctt atccaattca ttatgtcaat tcattaataa aataccttttt atgtagaggc      3600 tttatgttgc aattaaaaag ttgggaaaat gaaaaaaaaa aaaaaaaaaa aaaaaaaaaa      3660
aaaaaaaaaa aaaaaaaaaa aaaaaaaaaa aaaaaaaaa aaaaaaaaaa aaaaaaaaaa      3720
aaaaaaaaaa aaaaaaaaaa aaaaaaa                                          3747

<210> SEQ ID NO 7
<211> LENGTH: 1000
<212> TYPE: DNA
<213> ORGANISM: Homo sapiens
<220> FEATURE:
<221> NAME/KEY: misc_feature
<222> LOCATION: (500)..(500)
<223> OTHER INFORMATION: n = g or c

<400> SEQUENCE: 7
aaacaaagac taatgagttc ctagttagga aatattaata atcaaactag ctgaacatgt        60
agttatggta tttagtatat tgaaaactga ttgtcttgct ttatttaaat gcttgatacg       120
tttagtgaat attttttaagc ttattaagtc cctcttgtag aactagtatt taaagtttca       180
ataattgcct tgtagcaaaa attatggaac ctagatatcc taatggccat ttggttataa       240
tatagattct caataggtca tatggatatt tctgtttgga tctatgcctg ctttccttt       300 catggaggag aaggagcaga aggagttaat acctgaacag atataattgg ggctgcatca       360
aatacacata taaaaaagtc tatataagtg tactacttta aaatagtctt tttaaaaaaa       420
acttcacttt ttgaaaaact agtcaatcta atcaagtttg ttctgatgaa aaattgactt       480
ccttctctga ccttcattn tagcgagtag tccagtaaag tttgaatggg caagaaatgg       540
tcatcaaatc gtgaacttca caaatctcat aggctaaatt tcttaaaata tttgtatgca       600
atatgaataa ggcaggtgtc ttattcaaga aaagcaagta gtcattcaaa gtaaaacgta       660
tgctacttcc taaactgggc atatcatttg ctatgatttt tatttctgtg gatttggctt       720
tttatttttg ttttgagttt ttaattgcaa attcaaagca attaagcagg attataagca       780
acatatgcag catgttgctg agattttttac ttttttagcaa tcatccaaat ggatattgat       840
actagtaagg aaccaaatct aaaggtttat ttaaatgcaa atgattcaca gtttgaattt       900
taactaagaa caaaggaagg gacatttta agtggaattc agaatttaat caatgcaaat       960
tttcatttga ttatctgaaa catgcacaga agacccatgg                            1000

<210> SEQ ID NO 8
<211> LENGTH: 601
<212> TYPE: DNA
<213> ORGANISM: Homo sapiens
```

-continued

```
<220> FEATURE:
<221> NAME/KEY: misc_feature
<222> LOCATION: (301)..(301)
<223> OTHER INFORMATION: n = a or t

<400> SEQUENCE: 8
agggttcctg ggaggaatcc cgaggaaata gacgctgctg ctctgctgat tgtctccact      60
atcctgtttt gctcctaccc actaatccag cctgggaggc tctgggcatt agcggaaggc     120
ttcaccacaa ggagacagga gcgagtattc cataggcatg cgctcctagt ggcacgagtg    180
gcttgggtca ggatcaaaga gtgaaggatt cggaagtcag ctatctggag agagagagag    240
agagattgtg ttttattcgt gtcccatagc tttcctatcc tatccctatc ctagctttta    300
ncctgagcca gagctcacta cacaggttcc tggctatcga gtctgaatct gcactactca    360
acttataaac tgtctgcaga cacctgttag ggaaattgct gatcatgggc agcaggatct    420
gaactcgctt taccttctcg tttggagcac agggaccgcc cagctagagg agcaccagcg    480
cactgcgccc cagccctggg cgagggtgcg gaggatttgt tctcggtgca atcctgctgg    540
cgcttttccg gggttctgcg cggatccagc tccccatctc tgctcctaca cacacaaaag    600
a                                                                    601
```

COMPOSITIONS AND METHODS FOR OBESITY SCREENING USING POLYMORPHISMS IN NPY2R

RELATED APPLICATIONS

This application claims priority to U.S. Provisional Application No. 60/610,992, filed Sep. 17, 2004, the content of which is hereby incorporated by reference in its entirety.

FIELD OF THE INVENTION

The present invention is in the field of diagnosing metabolic disorders and therapy. In particular, the present invention relates to specific single nucleotide polymorphisms (SNPs) in the human genome, and their association with obesity and related pathologies.

BACKGROUND OF THE INVENTION

Obesity has reached epidemic proportions in the United States and developing countries. While the trend of decreased physical activity and increased caloric intake is probably responsible for the recent rise in obesity, it is important to understand that these trends are playing out on a background of genetic variation in the population. Each individual's genetic background remains an important determinant of susceptibility to obesity.

The obesity epidemic is due to dietary and behavioral trends acting on a person's genetic makeup to determine body mass and susceptibility to obesity related disease. Obesity has a strong hereditary component, yet genetic pathways that contribute to obesity have not yet been elucidated. Many genetic association studies have been reported, but few have been successfully replicated, and none have led to effective treatment of common obesity.

Obesity often tracks in families. Having obese relatives increases one's risk for obesity, even if the family members do not live together or share the same patterns of exercise and food intake. Family studies and twin studies yield estimates of the fraction of the variation in the population that can be attributed to inherited variation, or the heritability ($h^2$). Obesity is not inherited in families in a predictable pattern, but rather shows a complex pattern of segregation, indicating that multiple genes are involved. Because of this complex, multi-factorial pattern, diseases and traits such as obesity are called complex genetic traits. A few studies have suggested that there are genes that act in a recessive manner and can explain a larger fraction of the variation in body mass. These results have not been consistently observed, and may also reflect the patterns seen in early onset, severe obesity caused by one or few genes, rather than the more common polygenic, later onset obesity observed in the general population. Thus, each of the obesity genes likely makes only a small contribution to body weight, but together inherited variation plays a large role in determining how an individual responds to the environmental factors of diet and physical activity.

While humans all have the same basic genetic material, every person's genome is slightly different. In comparing any two copies of the same stretch of genome, about one in every 1200 bases will be different (usually a single nucleotide polymorphism, or SNP). Most SNPs identified by comparing two chromosomes are common, and shared throughout the world—90% of such SNPs will be seen again at a frequency of at least 1%. Most of these common variants probably have no functional consequence, and are essentially the equivalent of genetic dialect, or random differences in spelling with no real significance. However, a few of these polymorphisms will alter the biologic function of a gene, either by affecting the structure of the protein or by altering the location, amount or time at which the protein is made. Some of these functional alterations will affect susceptibility to obesity and related diseases. Hence, there is a need in the art to better identify these causal variants and their interaction with each other and environmental factors.

Accordingly, there exists a need in the art for methods of early detection and identification of high-risk individuals who are susceptible to developing abnormal body weight. There is also a need for compositions and methods that can modulate metabolism and/or treat obesity.

SUMMARY OF THE INVENTION

The disclosed naturally-occurring SNPs located upstream of the NPY2R gene can be used as targets for the design of diagnostic reagents and the development of therapeutic agents, as well as for disease association and linkage analysis. In particular, the SNPs of the present invention are useful for identifying an individual who is at an increased or decreased risk of developing metabolic disorders, such as obesity, and for early detection of the disease, for providing clinically important information for the prevention and/or treatment of metabolic disorder, and for screening and selecting therapeutic agents. The SNPs disclosed herein are also useful for human identification applications. Methods, assays, kits, and reagents for detecting the presence of these polymorphisms and their encoded products are provided.

The SNPs disclosed in the present invention are based on differences in allele frequencies in the obese patient population relative to normal weight individuals. The SNPs can be used to determine predisposition for a metabolic disorder that involves metabolic processes such as, but not limited to, lipid and lipoprotein concentrations, energy homeostasis, body weight, and body composition-parameters. Common diseases are associated with abnormalities in these metabolic processes, including, but not limited to, hypertriglyceridemia, atherosclerosis, obesity, diabetes, neuropsychiatric disease and insulin resistance.

In one aspect, the present invention relates to the identification of SNPs, unique combinations of such SNPs, and haplotypes of SNPs that are associated with metabolic disorders and related pathologies. The polymorphisms disclosed herein are directly useful as targets for the design of diagnostic reagents and the development of therapeutic agents for use in the diagnosis and treatment of obesity and related pathologies.

In another aspect, the present invention identifies biological markers for pinpointing a metabolic disorder on the human genome map. The identified SNPs are located near the NPY2R gene. The invention is intended to include SNPs that are in linkage equilibrium with the identified polymorphisms. In yet another aspect, the identified polymorphisms and/or combination of polymorphisms of the present invention can cause susceptibility to a metabolic disorder. In one embodiment, at least one of SEQ ID Nos. 1-5, 7-8 can lead to a misregulation (e.g., downregulation or upregulation) of NPY2R activity. For example, this misregulation can result from altered timing and/or amount of expression, altered structure, altered splice variants, or an altered transcription of NPY2R (e.g., SNPs in transcription factor binding domains, SNPs in promoter regions, in areas involved in transcript processing, such as SNPs at intron-exon boundaries that may cause defective splicing, or SNPs in mRNA processing signal sequences such as polyadenylation signal regions).

Based on the identification of SNPs associated with metabolic disorders, the present invention also provides methods of detecting these variants as well as the design and preparation of detection reagents. The invention provides SNPs in genetic sequences involved in obesity and diabetes, methods of detecting these SNPs in a test sample, methods of identifying individuals who have an altered (i.e., increased or decreased) risk of developing metabolic disorders, such as obesity and diabetes, based on the presence of a SNP disclosed herein or its encoded product, methods of identifying individuals who are more or less likely to respond to a treatment, methods of screening for compounds useful in the treatment of a metabolic disorder associated, compounds identified by these methods, methods of treating metabolic disorders, and methods of using the novel SNPs of the present invention for human identification.

In one embodiment of the present invention, naturally-occurring SNPs in the human genome are provided. These SNPs, SEQ ID Nos. 1-5 and 7-8, are associated with metabolic disorders such that they can have a variety of uses in the diagnosis and/or treatment of obesity.

One aspect of the present invention relates to an isolated nucleic acid molecule comprising a nucleotide sequence in which at least one nucleotide is a SNP disclosed in SEQ ID Nos. 1-5, and 7-8. In an alternative embodiment, a nucleic acid of the invention is an amplified polynucleotide, which is produced by amplification of a SNP-containing nucleic acid template. In another embodiment, the invention provides for a variant protein which is encoded by a nucleic acid molecule containing a SNP disclosed herein.

In yet another embodiment of the invention, a reagent for detecting a SNP in the context of its naturally-occurring flanking nucleotide sequences (which can be, e.g., either DNA or mRNA) is provided. In particular, such a reagent may be in the form of, for example, a hybridization probe or an amplification primer that is useful in the specific detection of a SNP of interest. In an alternative embodiment, a protein detection reagent is used to detect a variant protein which is encoded by a nucleic acid molecule containing a SNP disclosed herein. A preferred embodiment of a protein detection reagent is an antibody or an antigen-reactive antibody fragment.

Also provided in the invention are kits comprising SNP detection reagents, and methods for detecting the SNPs disclosed herein by employing detection reagents. In a specific embodiment, the present invention provides for a method of identifying an individual having an increased or decreased risk of developing a metabolic disorder, such as obesity and diabetes, by detecting the presence or absence of a SNP allele disclosed herein. In another embodiment, the invention provides a method of diagnosis of a metabolic disorder by detecting the presence or absence of a SNP allele disclosed herein.

The nucleic acid molecules of the invention can be inserted in an expression vector, such as to produce a variant protein in a host cell. Thus, the present invention also provides for a vector comprising a SNP-containing nucleic acid molecule, genetically-engineered host cells containing the vector, and methods for expressing a recombinant variant protein using such host cells. In another specific embodiment, the host cells, SNP-containing nucleic acid molecules, and/or variant proteins can be used as targets in a method for screening and identifying therapeutic agents or pharmaceutical compounds useful in the treatment of obesity.

An aspect of this invention is a method for treating a metabolic disorder in a human subject wherein said human subject harbors a gene, transcript, and/or encoded protein identified by SEQ ID Nos. 1-5, and 7-8, which method comprises administering to the human subject a therapeutically or prophylactically effective amount of one or more agents counteracting the effects of the disease, such as by inhibiting (or stimulating) the activity of the gene, transcript, and/or encoded protein.

Another aspect of this invention is a method for identifying an agent useful in therapeutically or prophylactically treating metabolic disorders in a human subject where the human subject harbors a gene, transcript, and/or encoded protein identified herein. The method comprises contacting the gene, transcript, or encoded protein with a candidate agent under conditions suitable to allow formation of a binding complex between the gene, transcript, or encoded protein and the candidate agent and detecting the formation of the binding complex, wherein the presence of the complex identifies said agent.

Other features and advantages of the invention will become apparent to one of skill in the art from the following detailed description, the drawings, and from the claims.

BRIEF DESCRIPTION OF THE DRAWINGS

FIG. 4 is a table summarizing the results of the case studies showing an association between several SNPs in NPY2R, encoding the NPY receptor type 2, and obesity in men;

FIG. 6 is a chart of statistical data from five NPY2R SNPs associated with obesity in men;

FIG. 9 is a chart of statistical data from four haplotypes in NPY2R;

FIG. 10 is a chart relating BMI in Scandinavian trios to five SNPs in NPY2R;

FIG. 11 is a chart of combined statistical data from European derived populations;

FIG. 12 showing statistical data from the African American population group.

DETAILED DESCRIPTION OF THE INVENTION

Figure 1:
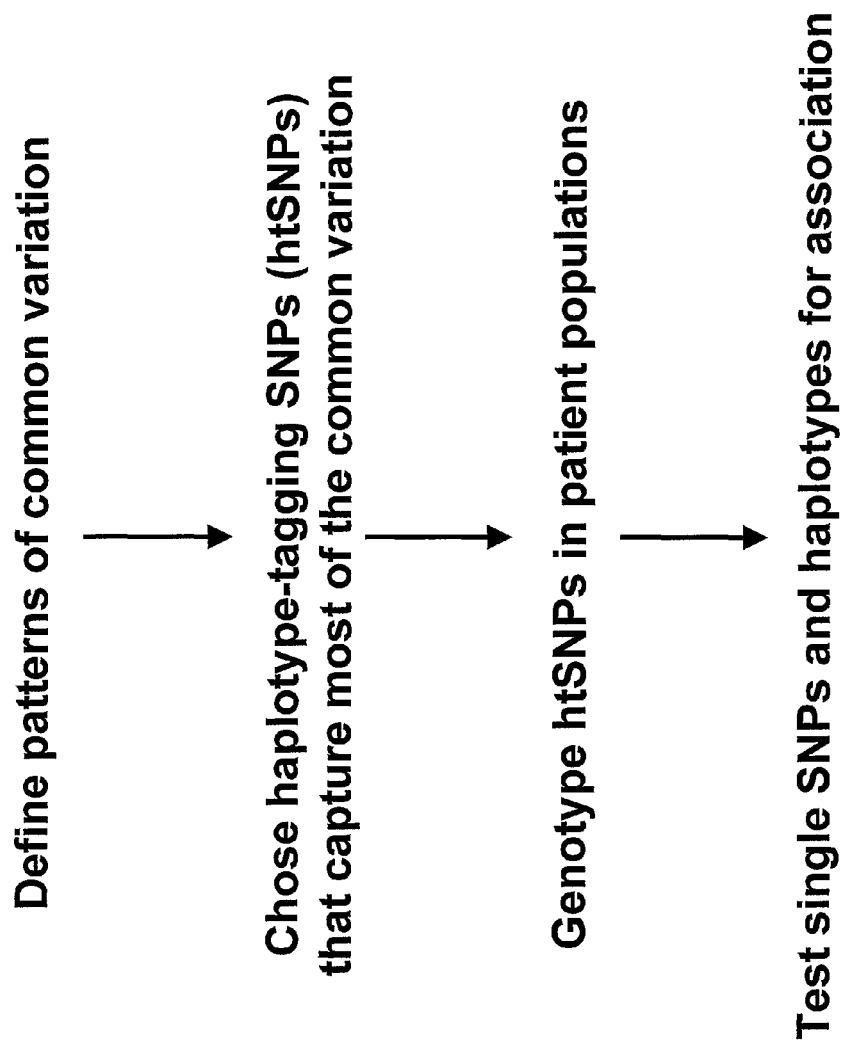
FIG. 1 is an overview of the experimental design of the experiments detailed in the Examples section.

The practice of the present invention employs, unless otherwise indicated, conventional methods of analytical biochemistry, microbiology, molecular biology and recombinant DNA techniques within the skill of the art. Such techniques are explained fully in the literature.

The terminology used herein is for describing particular embodiments and is not intended to be limiting. Unless defined otherwise, all scientific and technical terms are to be understood as having the same meaning as commonly used in the art to which they pertain. For the purposes of the present invention, the following terms are defined below:

As used herein, a "metabolic disorder" includes a disease, disorder, or condition which is associated with abnormal or aberrant body weight. The National Institute of Health defines normal body weight as a body mass index (BMI) between about 18.5 to about 24.9 kg/m². The present invention is intended to include disorders characterized by a body mass index (BMI) outside (i.e., lower than or higher than) the normal range. The National Institute of Health defines obesity as a body mass index (BMI) of 30 kg/m² or more and overweight as a BMI of 25.0 to 29.9 kg/m². In a preferred embodiment, the metabolic disorder is characterized by a subject with a BMI of about 25 kg/m² or more. A metabolic disorder can result from aberrant thermogenesis, energy expenditure, and or lipid and lipoprotein concentrations. Metabolic disorders are also intended to include both disorders directly related to abnormal body weight, such as, but not limited to, obesity, overweight, anorexia, and diseases that are secondary to abnormal body weight, such as, but not limited to, hypertriglyceridemia, hypertension, atherosclerosis, diabetes, cardiovascular disease, neuropsychiatric diseases and insulin resistance.

As used interchangeably herein, "NPY2R activity," "biological activity of NPY2R" or "functional activity of NPY2R," includes an activity exerted by a NPY2R protein, polypeptide or nucleic acid molecule on a NPY2R responsive cell or tissue or on a NPY2R protein substrate, as determined in vivo, or in vitro, according to standard techniques. NPY2R activity can be a direct activity, such as an association with a NPY2R-target molecule. As used herein, a "substrate" or "target molecule" or "binding partner" is a molecule with which a NPY2R protein binds or interacts in nature, such that NPY2R-mediated function, e.g., modulation of appetite, is achieved. A NPY2R target molecule can be a non-NPY2R molecule (e.g., NAD+, NADP+, or other cofactor, or a biochemical molecule involved in modulating NPY2R activity), or a NPY2R protein or polypeptide. Examples of such target molecules include proteins in the same signaling path as the NPY2R protein, e.g., proteins which may function upstream (including both stimulators and inhibitors of activity) or downstream of the NPY2R protein in a pathway involving regulation of appetite or body weight. Alternatively, a NPY2R activity is an indirect activity, such as a cellular signaling activity mediated by interaction of the NPY2R protein with a NPY2R target molecule. The biological activities of NPY2R can include, for example, one or more of the following activities: 1) they modulate metabolism or catabolism of biochemical molecules; 2) they modulate establishment/maintenance of hypertension induced by aortic coarctation; 3) they modulate diabetic retinopathy and retinal neovascularization; 4) they modulate release of multiple neurotransmitters in mammalian retina (i.e., through voltage-dependent $Ca^{+2}$ influx into rod bipolar cell terminal); 5) they modulate anxiety-related and stress related behavior (such as through GABA and glutamate in the brain); 6) they modulate energy homeostasis and/or energy expenditure; 7) they modulate insulin sensitivity 8) they modulate leptin action; and 9) they modulate bone loss; 10) they modulate body weight and/or food intake; and 11) they modulate neuropsychiatric disease.

The term "NPY2R," as used herein, refers to a member of the family of G-protein-coupled receptors that interact with neuroendocrine peptides. NPY receptors are a family of G protein-coupled receptors for neuroendocrine peptides such as neuropeptide Y (NPY), peptide YY (PYY), and pancreatic polypeptide (PP). Neuropeptide Y (NPY), peptide YY (PYY) and pancreatic polypeptide (PP) can exert their effects through the NPY2 receptors, which are located on intrinsic neurons as well as epithelia in colon mucosa. The NPY receptors are present throughout the central and peripheral nervous systems and function in the regulation of appetite, blood pressure, mood, release of pituitary hormones, and circadian rhythms. For example, NPY, a 36-amino-acid peptide widely expressed in the brain, has been related to physiological responses, including hypothalamic control of food intake and cardiovascular homeostasis. At least six human NPY receptors have been identified (NPY1R 4q31.3-q32 (170 cM), NPY2R 4q31 (164 cM), PPYR1 10q11.2-q21.2, NPY5R 4q31.3-q32 (170 cM), and NPY6R 5q31 8). The human sequence of NPY2R, neuropeptide Y receptor Y2, is contained in SEQ ID No. 6. (GenBank Accession No. NM_000910.2; GI:27552771).

The term "modulate" or "modulator," as used herein, refers to a change in activity of NPY2R. For example, modulation can cause an increase or decrease in protein activity, binding characteristics, or any other biological or functional property of NPY2R. For example, the change in activity is at least a change of 2% from the normal or standard activity of NPY2R. Preferably, the change in activity is at least a change of 5% from the normal or standard activity of NPY2R.

As used herein, an "isolated nucleic acid molecule" refers to one that contains a SNP of the present invention or one that hybridizes to such molecule such as a nucleic acid with a complementary sequence, and is separated from some other nucleic acids present in the natural source of the nucleic acid molecule. Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. A nucleic acid molecule can be fused to other coding or regulatory sequences and still be considered "isolated." Nucleic acid molecules present in non-human transgenic animals, which do not naturally occur in the animal, are also considered "isolated." For example, recombinant DNA molecules contained in a vector are considered "isolated." Further examples of "isolated" DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

An isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position.

For full-length genes and entire protein-coding sequences, a SNP flanking sequence can be, for example, up to about 7 KB, 6 KB, 5 KB, 4 KB, 3 KB, 2 KB, or 1 KB on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Polymorphic genomic sequences are provided in the Sequence Listing (SEQ ID Nos:1-5, 7-8). Furthermore, fragments of such full-length genes and transcripts that contain one or more SNPs disclosed herein are also encompassed by the present invention, and such fragments may be used, for example, to express any part of a protein, such as a particular functional domain or an antigenic epitope.

An isolated nucleic acid molecule of the present invention further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a SNP disclosed herein. Such primers may be used to amplify DNA of any length so long that it contains the SNP of interest in its sequence.

As used herein, an "amplified polynucleotide" of the invention is a SNP-containing nucleic acid molecule whose amount has been increased at least two fold by any nucleic acid amplification method performed in vitro as compared to its starting amount in a test sample. In other preferred embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, or 300 nucleotides in length. While the total length of an amplified polynucleotide of the invention can be as long as an exon, an intron or the entire gene where the SNP of interest resides, an amplified product is typically no greater than about 1,000 nucleotides in length (although certain amplification methods may generate amplified products greater than 1000 nucleotides in length). More preferably, an amplified polynucleotide is not greater than about 600 nucleotides in length. It is understood that irrespective of the length of an amplified polynucleotide, a SNP of interest may be located anywhere along its sequence.

The term "subject," as used herein, refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult, children, and newborn subjects, as well as fetuses, whether male or female, are intended to be covered.

I. SNPs

The genomes of all organisms undergo spontaneous mutation in the course of their continuing evolution, generating variant forms of progenitor genetic sequences. A variant form may confer an evolutionary advantage or disadvantage relative to a progenitor form or may be neutral. In some instances, a variant form confers an evolutionary advantage to the species and is eventually incorporated into the DNA of many or most members of the species and effectively becomes the progenitor form. Additionally, the effects of a variant form may be both beneficial and detrimental, depending on the circumstances. For example, a heterozygous sickle cell mutation confers resistance to malaria, but a homozygous sickle cell mutation is usually lethal. In many cases, both progenitor and variant forms survive and co-exist in a species population. The coexistence of multiple forms of a genetic sequence gives rise to genetic polymorphisms, including SNPs.

Approximately 90% of all polymorphisms in the human genome are SNPs. SNPs are single base positions in DNA at which different alleles, or alternative nucleotides, exist in a population. The SNP position (interchangeably referred to herein as SNP, SNP site, or SNP locus) is usually preceded by and followed by highly conserved sequences of the allele (e.g., sequences that vary in less than {fraction (1/100)} or {fraction (1/1000)} members of the populations). An individual may be homozygous or heterozygous for an allele at each SNP position. A SNP can, in some instances, be referred to as a "cSNP" to denote that the nucleotide sequence containing the SNP is an amino acid coding sequence.

A SNP may arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion or deletion variant referred to as an "indel."

A synonymous codon change, or silent mutation/SNP (terms such as "SNP," "polymorphism," "mutation," "mutant," "variation," and "variant" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers," or "di-allelic markers."

As used herein, references to "SNPs" and SNP genotypes include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases.

Causative SNPs are those SNPs that produce alterations in gene expression or in the expression, structure, and/or function of a gene product, and therefore are most predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Such variant products can result in a pathological condition, e.g., genetic disease. Examples of genes in which a SNP within a coding sequence causes a genetic disease include sickle cell anemia and cystic fibrosis.

Causative SNPs do not necessarily have to occur in coding regions; causative SNPs can occur in, for example, any genetic region that can ultimately affect the expression, structure, and/or activity of the protein encoded by a nucleic acid. Such genetic regions include, for example, those involved in transcription, such as SNPs in transcription factor binding domains, SNPs in promoter regions, in areas involved in transcript processing, such as SNPs at intron-exon boundaries that may cause defective splicing, or SNPs in mRNA processing signal sequences such as polyadenylation signal regions. Some SNPs that are not causative SNPs nevertheless are in close association with, and therefore segregate with, a disease-causing sequence. In this situation, the presence of a SNP correlates with the presence of, or predisposition to, or an increased risk in developing the disease. These SNPs, although not causative, are nonetheless also useful for diagnostics, disease predisposition screening, and other uses.

An association study of a SNP and a specific disorder involves determining the presence or frequency of the SNP allele in biological samples from individuals with the disorder of interest, such as a metabolic disorder, and comparing the information to that of controls (i.e., individuals who do not have the disorder; controls may be also referred to as "healthy" or "normal" individuals) who are preferably of similar age and race. The appropriate selection of patients and controls is important to the success of SNP association studies. Therefore, a pool of individuals with well-characterized phenotypes is extremely desirable.

A SNP may be screened in diseased tissue samples or any biological sample obtained from a diseased individual, and compared to control samples, and selected for its increased (or decreased) occurrence in a specific pathological condition, such as pathologies related to obesity. Once a statistically significant association is established between one or more SNP(s) and a pathological condition (or other phenotype) of interest, then the region around the SNP can optionally be thoroughly screened to identify the causative genetic locus/sequence(s) (e.g., causative SNP/mutation, gene, regulatory, region, etc.) that influences the pathological condition or phenotype as shown in the Examples. Association studies can be conducted within the general population and are not limited to studies performed on related individuals in affected families (linkage studies).

Clinical trials have shown that patient response to treatment with pharmaceuticals is often heterogeneous. There is a continuing need to improve pharmaceutical agent design and therapy. In that regard, SNPs can be used to identify patients most suited to therapy with particular pharmaceutical agents (this is often termed "pharmacogenomics" or "pharmacogenetics").

Similarly, SNPs can be used to exclude patients from certain treatment due to the patient's increased likelihood of developing toxic side effects or their likelihood of not responding to the treatment. Pharmacogenomics can also be used in pharmaceutical research to assist the drug development and selection process. For example, in one aspect of the invention the NPY2R haplotype GACAGAA was shown to be associated with protection from diabetes ($p=6.53\times10^{-4}$, odds ratio 0.78, 95% confidence interval 0.67-0.90). For example, the presence of a genetic polymorphism characterized by the presence of at least one genetic variation, wherein the genetic polymorphism is selected from the group consisting of G at position 156702170, A at position 156702331, C at position 156702960, A at position 156703137, G at position 156706216, A at position 156706671, and A at position 156706781 on chromosome 4, or those in linkage disequilibrium therewith, is associated with protection (or decreased risk) of type 2 diabetes and/or obesity. In another embodiment, the presence of a genetic polymorphism characterized by the presence of G at position 156702170 and at least one additional genetic polymorphism selected from the group consisting of A at position 156702331, C at position 156702960, A at position 156703137, G at position 156706216, A at position 156706671, and A at position 156706781 on chromosome 4, or those in linkage disequilibrium therewith, is associated with protection (or decreased risk) of type 2 diabetes and/or obesity.

II. Genetics of Obesity

The types of variants (missense or regulatory, rare or common), that affect complex traits such as obesity are being explored. Because most human genetic variation is common, it has been proposed based on theoretic and empirical grounds that common variants contribute to common disease and complex traits. However, rare variants have also been proposed to play a role. The relative importance of missense variants has been debated as well. Ideally, in order to have an unbiased and comprehensive search for variants with a contributory role to obesity we would test every variant in the genome, but such a large-scale search through even just the common variants (of which there are estimated to be 11 million) is not yet practical. The present invention identifies genomic regions, 0.6 to 5 kb upstream of the NPY2R gene, and sets of variants that are contribute to obesity.

Two approaches have been used to find the variants that affect obesity, linkage analysis and association studies. Linkage analysis has been used with great success in mapping genes responsible for single gene disorders. Such studies involve using multiple affected relatives to look for shared segments of DNA that are inherited more often than expected by chance, eventually narrowing the shared region to a few genes that can be tested for the presence of recognizable mutations in all of the affected relatives. Linkage studies have been applied to complex disorders such as obesity, but in general, linkage analysis has been less successful for these multigenic diseases. While whole genome scans often identify similar regions as being linked to obesity, the results vary greatly, probably due to the low power of linkage to find genes with modest effects, or possibly differing study designs or populations. Several studies located a region on chromosome 7q31 that was found to contain the leptin gene, mutations in which cause severe obesity syndromes. While some regions have been repeatedly implicated by linkage analysis, prior to this invention, no genes have been found in these regions that have been seen to contribute to common obesity.

Association studies are another way to find genes involved in obesity. Genes and variants are selected as candidates either due to a known or hypothesized role in metabolism, or due to their location within an area of linkage. In the simplest form of such studies, the frequency of a variant allele in a particular gene is compared in obese and non-obese individuals, or in obese individuals and their non-obese relatives. Association studies to test these functional and positional candidates have better power than linkage studies to detect the effects of common alleles of modest penetrance on complex traits such as obesity.

Association studies have been successfully used to identify genes for common diseases and complex traits. An example of a now well established disease association is that of Alzheimers disease with the gene encoding the apolipoprotein E (ApoE). Prior to this invention, many other associations have been reported, including for obesity, but few have been consistently reproducible as is seen with ApoE4 and Alzheimer's Disease.

There are several possible reasons that association studies are not replicated consistently, and it is critical to discern which is present when interpreting association studies. To explore this issue, a meta-analysis of published association studies by pooling the results from all of the follow-on studies for 25 reported associations between common genetic variants and common diseases (Lohmueller K E, Pearce C L, Pike M, Lander E S, Hirschhorn J N. Meta-analysis of genetic association studies supports a contribution of common variants to susceptibility to common disease. *Nat Genet* 2003;33: 177-82). Most of these associations showed no evidence of replication in the follow-on studies. Eight of the associations showed convincing evidence of replication, and for these the associated variant conferred a modest effect with a less than two-fold increase in disease risk. Most association studies are therefore incorrect. A fraction of reported associations are likely to be correct, yet difficult to replicate with small studies that are underpowered to detect a modest effect.

The present invention identifies polymorphisms located 0.6 to 5.0 kb upstream of the NPY2R gene that are associated with obesity. Abundant genetic variants (dbSNP) and patterns of common variation elucidated by the human HapMap has facilitated the selection of variants tested in association studies. (See Example 1).

In one embodiment, risk of obesity is correlated with the presence of the GGAGAAG haplotype on chromosome 4, upstream of NPY2R. This haplotype was found with 31% frequency in a reference European-American population. The combined U.S., Polish, Framingham heart study, and Scandinavian male populations and showed an association with obesity (n>2440, p=1.86×10$^{-4}$, odds ratio=1.27, 95% confidence interval 0.95-1.27). As shown in the examples, risk of obesity is associated with at least one genetic polymorphism selected from the group consisting of G at position 156702170, G at position 156702331, A at position 156702960, G at position 156703137, A at position 156706216, A at position 156706671, and G at position 156706781 on chromosome 4, or those in linkage disequilibrium therewith.

III. Identification of Genes and Pathways Associated with Metabolic Disorders

Metabolic disorders are complex genetic disorders that are caused by multiple genes as well as environmental triggers. Using the traditional approaches of human genetics, little progress was made towards understanding these root causes of human disease. Recently, however, there have been dramatic increases in knowledge of the human genome and its variation. These advances, combined with automated data collection and analytic improvements, have made possible for the first time systematic testing of candidate genes for a role in disease. This invention is based, in part, on efficient use of these new tools, sparked by selection of the most likely candidate genes to test, and large samples and analytic rigor to achieve robust results.

High priority candidate genes for obesity were selected and their genetic variation in 2,000 patient samples with extremes of body mass index were comprehensively tested. These data were be analyzed for associations with obesity, with any associations tested for replication and further characterized in an additional set of 2,650 patient samples with extremes of BMI and waist-hip ratio as shown in Example 1.

Obesity, the major risk factor for type 2 diabetes (T2DM), has become an epidemic public health problem, with profound consequences on morbidity and mortality from type 2 diabetes. Obesity (as measured by body mass index, or BMI) confers a 3- to 10-fold increased risk of T2DM and is increasing rapidly. This rise in obesity is seen in children as well, suggesting that a future epidemic of type 2 diabetes is looming. Although changing environmental factors such as diet and exercise are responsible for the recent rise in mean body weight, where an individual lies within this population distribution is strongly influenced by genetic background. Moreover, achieving weight loss through modification of environmental factors and behavior has proven difficult. Thus, understanding the genetic factors that lead to increased risk of obesity is critical to identifying the pathways by which obesity develops in humans in our current environment. Such knowledge would guide the search more effective interventions to prevent obesity and its sequellae, primarily type 2 diabetes.

Body mass index (BMI) is a highly heritable predictor of diabetes, but none of the genes affecting BMI are known. Twin and family studies have shown that approximately 50% of the variability in BMI is due to genetic factors: some people have a genetic predisposition to become obese in an environment of low activity and abundant calories, while others do not. Because BMI is heritable, can be measured comparably and accurately across populations, and is a strong predictor of diabetes, BMI was the focus of this study, even though it is not a direct measure of fat mass. An alternate obesity-related phenotype, abdominal obesity (waist circumference or waist-hip ratio) is also highly heritable and a independent strong predictor of diabetes. Like diabetes, obesity is a complex genetic trait.

Genome-wide linkage analysis has identified multiple regions of confirmed linkage, primarily to BMI, but no causal gene has yet been found prior to this invention. Regions observed with genome-wide significance and supported by multiple studies include 3q21-q22, 3q26-q27, 6q23-q24, 6q26-q27, 7q31-q33, 10p12-p11, 11q23-q24, and 20p11-20q12. These regions likely represent confirmed locations of genes influencing obesity, however, no specific genes had been discovered prior to this invention. This is likely because the linked regions are large, and contain many genes. The genomic information and technology to take on such a problem has only recently become available. And, importantly, it was necessary to integrate across multiple data types to efficiently sort through the large number of genes in each such region. Thus, these regions provided important clues to the location of genes with potentially large effects on obesity.

Resequencing of candidate genes, looking for missense variants that affect disease, is currently very costly and labor-intensive, since each exon of each candidate gene must be screened in every patient.

Until recently, association studies were limited by knowledge of human genes, the number of available genetic markers, and ability to genotype these markers in adequately sized samples. Association studies offer the most powerful method to test variation in a gene for a role in disease. Association studies require, at a minimum, knowledge of the gene, a sufficient number of genetic markers comprehensively to survey the variation present in the gene, and the ability to type these markers in arbitrarily large and well-phenotyped patient samples. Recently, methods have been developed and implemented that largely overcome each of these previous limitations on performing comprehensive association studies.

Furthermore, over the last few years, the human genome sequence has become available, and abundant single nucleotide polymorphisms (SNPs) have been discovered that can serve as genetic markers to help locate and map disease genes. Recent studies have shown that the genome can be parsed into "blocks" of linkage disequilibrium, within which genetic variants show strong correlation with each other. Numerous methods to rapidly genotype SNPs have been developed and implemented. These methods make it possible to comprehensively test for association between genotype and phenotype at any given gene locus. Within such blocks, there were only a few common arrangements of alleles at consecutive markers (haplotypes), and these common haplotypes accounted for 90% of all the chromosomes in the population. The human genome is characterized generally by haplotype blocks—65-85% of the genome sequence is spanned by long (>10 kb) blocks with limited haplotype diversity. Within haplotype blocks, SNPs that tag each haplotype (htSNPs) can serve as proxies for the vast majority of common variation within the block, decreasing the number of markers required to comprehensively survey each region.

Large number of DNA samples were assembled from individuals at the near-extremes of body mass index, an extremely powerful and efficient design for studying quantitative traits. These samples include a well-powered set for screening for associations with BMI: 1300 obese ($90^{th}$-$97^{th}$ percentile) and 700 lean ($5^{th}$-$12^{th}$ percentile) U.S. Caucasians. This sample provides adequate power to identify variants that contribute much less than 1% of the total variation in BMI. To follow up associations seen in the screening sample, the laboratory has a similar sample of 700 obese and 330 lean individuals from Poland. To further refine any variants found to be associated with altered BMI, a collection of 350 parent-offspring trios were assembled where the offspring have extremes of waist-hip ratio (abdominal obesity) for which BMI was also collected. Specifically, these non-diabetic individuals were selected from a large clinic population as having sex-adjusted WHR that was in the top 10% or bottom 20% of the population distribution. As with BMI (above), samples drawn from the tails of the distribution are maximally efficient for genetic studies of quantitative traits (See FIGS. 10-11).

There are several well-established reproducible associations of common variants with disease risk, but many more reported associations have not been consistently replicated, including associations to diabetes and obesity. A critical question in interpreting association studies is to understand the source of this inconsistency. To address this question, 25 different reported associations were analyzed, all of which had been studied multiple times but with inconsistent results, to determine whether there was evidence that any of these represented true associations. A marked excess ($P<10^{-14}$) of replications could not be explained by publication bias or other confounders. Critically, for the associations that were confirmed in the meta-analysis, the estimated genetic effects were modest, and would be difficult to detect in small studies. This meta-analysis strongly supports the idea that multiple, large samples are essential to test genetic variants for association, and we have taken this approach in our effort to identify the variants that contribute to diabetes and obesity in human patients.

To directly connect high priority genes with human diabetes and obesity, variation at these genes were comprehensively characterized to identify a set of variants that efficiently captures this variation, and these variants were tested for association to diabetes or obesity in large patient samples as described below.

Selection of candidate of genes for obesity. Genes will be selected that can be tied to obesity with functional data from model systems and data from patients. This process incorporated data from multiple sources, including model systems such as *C. elegans*, regions of confirmed linkage to BMI, and genetic data from linkage studies in mouse.

The initial list of genes for obesity included genes identified in *C. elegans* that lie in regions of confirmed linkage to obesity. By integrating the lists from *C. elegans* RNAi screen for fat content with regions of confirmed linkage to BMI, we identified genes as initial candidates. These include PCK1 (phosphoenolpyruvate carboxykinase), a main regulatory target for gluconeogenesis and glyceroneogenesis, DRD2 (pituitary D2 dopamine receptor), ACAS2 (acetyl-Coenzyme A synthetase 2), a SREBP-regulated gene in fatty acid metabolism, QPCT (pituitary glutaminyl-peptide cyclotransferase), involved in processing of secreted neuropeptides, and TPT (trans-prenyltransferase), involved in processing coenzyme Q in the OXPHOS pathway. Interestingly, many of these genes have additional evidence for a role in obesity; for example, deletion of a PPARG responsive element upstream of PCK1 reduces fat content in mice.

Characterization of variation in high priority genes. To efficiently survey variation in high priority genes, common haplotypes were defined across each selected gene using a haplotype-based approach. The ongoing HapMap project was used for data on common haplotypes throughout the entire genome. Using the Hap Map data (as well as any additional genotyping that we deem necessary for completeness), regions of strong linkage disequilibrium were identified using algorithms we previously described (Gabriel et al. 2002 The structure of haplotype blocks in the human genome. *Science* 296:2225-9). At least 6 polymorphic SNPs per block were used to be certain that the common haplotypes were well characterized. Within each block, the common (>5%) haplotypes was defined with the standard Expectation-Maximization (EM) algorithm (Excoffier and Slatkin 1995 Maximum-likelihood estimation of molecular haplotype frequencies in a diploid population. *Mol Biol Evol* 12:921-7), as implemented in the Haploview software package developed by our co-applicant Mark Daly.

Within blocks of linkage disequilibrium, subsets of SNPs were identified that efficiently tag the common-haplotypes (htSNPs). As described above, sets of SNPs can be identified that mark the common haplotypes (>5%) within blocks and thereby capture the vast majority of common variation in well-characterized blocks. This set of tag SNPs was selected using a different feature of the Haploview software package. The set of tag SNPs is selected as the minimal set that can be used to accurately distinguish all haplotypes above a given frequency threshold. 5% was used as the threshold, since above this frequency we have both good power to identify the haplotypes and to test them for association in our samples.

The haplotype information was supplemented by identifying missense variants. To ensure that any potentially functional missense variants were identified, the coding regions of these genes were resequenced. Any missense polymorphisms that were present at more than 1% frequency were genotyped in the characterization panel to determine their relationship to the common haplotypes across each gene. On average 1-2 such missense SNPs per gene was found, although many of these were redundant with SNPs used to define haplotypes.

This resequencing effort were done using pipelines for automated alignment of coding regions to the genome, PCR primer design from genomic sequence, and primer ordering. PCR primers were characterized on a set of 3 DNAs, and primer pairs passing characterization will be used for sequencing. Sequencing was done using post-PCR clean up (shrimp alkaline phosphatase and Exonuclease I), and detection (use of ABI 3730 sequencers), resulting in an average Phred score of approximately 40 in the targeted regions, with 85%-90% of reads passing quality control thresholds. This extremely high quality was easily adequate for SNP discovery.

Genotyping. An efficient mass spectrometry-based genotyping method (MassArray) was used. SNP genotyping was performed as described by Gabriel et al. 2002 (Gabriel S B et al. (2002) The structure of haplotype blocks in the human genome. *Science* 296:2225-9), with up to 7 SNPs analyzed per well to achieve cost efficiency. Briefly, PCR primers for multiplex PCR were designed with short tails to avoid overlap in mass with primer extension products. PCR products were treated with shrimp alkaline phosphatase to inactivate excess nucleotides. Extension primers that hybridize adjacent to the SNP of interest are added, along with Thermosequenase and a mix of deoxy- and dideoxynucleotides such that the extension products corresponding to the two alleles will have different lengths and hence different masses. Products were spotted onto chips for automated MALDI-TOF mass spectrometry analysis to determine genotypes based on mass spectra. Genotypes were called automatically by software provided by Sequenom, with additional custom post-processing software available if needed. Genotyping error rate were estimated for each assay using apparent inheritance errors in parent-offspring trios, and discrepancies between replicate samples in non-trio samples. SNPs passed quality control if >80% of genotypes were successfully determined, with an error rate of <1%, and no violation of Hardy-Weinberg equilibrium (P>0.01).

Association studies for obesity and diabetes. Genes were screened for association to body mass index in a sample of 1300 obese and 700 lean individuals. For each high priority candidate gene, the htSNPs and missense SNPs were genotyped in a screening sample of U.S. Caucasians drawn from the $5^{th}$-$12^{th}$ percentile and $90^{th}$-$97^{th}$ percentile, based on percentile data from healthy controls in each gender and decade of life. The samples were drawn from a collection of 60,000 samples, comprising healthy controls and individuals with a diversity of diseases, including diabetes, heart disease, and other complications of obesity. As expected, the prevalence of diabetes in the obese population is high but is essentially absent in the lean population. The study included both obese diabetic individuals and obese individuals without diabetes, which allowed for separate associations with obesity and diabetes versus obesity alone. Significance was assessed using a chi-square test as described above. SNPs or haplotypes were considered to be preliminarily associated with BMI if the nominal P value is <0.05. Treating BMI as a dichotomous trait, this sample provided excellent power. For example >80% power was used to detect the effect of a 5% allele with a 1.5-fold increased risk of obesity or a 25% allele with a 1.25-fold increased risk. If BMI is considered as a quantitative trait, the study design is better powered, since the controls were taken from near the opposite end of the population distribution. In this circumstance, we had >80% power to detect associations that explain well under 1% of the total population variance in BMI.

Preliminary associations were followed up in an additional 4,650 samples. Any SNP with a nominal association to BMI in the screening sample was genotyped in the following additional sample: 700 obese and 300 lean individuals from Poland (also $5^{th}$-$12^{th}$ and $90^{th}$-$97^{th}$ percentile). These samples had similar power to the screening study and were used to confirm the original association. In addition, associations were explored with abdominal obesity in 350 parent-offspring trios where the offspring is in either the top 20% or bottom 10% for waist-hip ratio for which BMI data was collected. For this family-based sample, TDT was used for the low and high BMI samples, combining them as described in TDTQ4 by Allison (Allison D B (1997) Transmission-disequilibrium tests for quantitative traits. *Am J Hum Genet* 60:676-90). Any variants that were associated with BMI were also tested for an association with diabetes, using a 1000 case-control pair screening sample from Scandinavia.

Population stratification in the BMI samples was also assessed. Although lean and obese samples from the US and Poland are matched by the country of origin of their grandparents, it is possible that there is population stratification that could lead to false positives. 50 random markers were typed and standard methods were used to identify and correct for stratification, if it existed.

IV. Uses of SNPs Associated with Metabolic Disorders

In one aspect, the invention provides methods or screening assays for identifying modulators, i.e., candidate or test compounds or agents (e.g., peptides, peptidomimetics, small molecules, ribozymes, or NPY2R antisense molecules) which bind to NPY2R proteins, have a stimulatory or inhibitory effect on NPY2R expression or NPY2R activity, or have a stimulatory or inhibitory effect on the expression or activity of a NPY2R target molecule. Compounds identified using the assays described herein may be useful for treating metabolic disorders.

In another aspect, the invention provides methods of diagnosing or prognosing development of progression of a metabolic disorder in a subject, comprising detecting the presence of at least one genetic variation, wherein at least one such genetic variation is located about 0.6 to about 5.0 kb upstream of NPY2R gene on chromosome 4. The genetic variation is at least one of a polymorphism G/C at position 156702170, A/G mutation at position 156702331, a polymorphism A/C mutation at position 156702960, a polymorphism A/G mutation at position 156703137, a polymorphism A/G mutation at position 156706216, a polymorphism A/T at position 156706671 or a polymorphism A/G mutation at position 156706781 on chromosome 4 in the subject, wherein the presence of the mutation is indicative of the subject being predisposed to a metabolic disorder or predisposed for being protected from developing a metabolic disorder. The genetic variation can comprise a portion of SEQ ID No. 1, SEQ ID No. 2, SEQ ID No. 3, SEQ ID No. 4, SEQ ID No. 5, SEQ ID No. 7, or SEQ ID No. 8.

As used herein, the term "diagnose," includes, but is not limited to any of the following: detection of metabolic disorders that an individual may presently have, predisposition screening (i.e., determining the increased risk of an individual in developing a metabolic disorders in the future, or determining whether an individual has a decreased risk of developing metabolic disorders in the future), determining a particular type or subclass of metabolic disorders in an individual known to have obesity, confirming or reinforcing a previously made diagnosis of a metabolic disorder, pharmacogenomic evaluation of an individual to determine which therapeutic strategy that individual is most likely to positively respond to or to predict whether a patient is likely to respond to a particular treatment, predicting whether a patient is likely to experience toxic effects from a particular treatment or therapeutic compound, and evaluating the future prognosis of an individual having a metabolic disorders. Such diagnostic uses are based on the SNPs individually or in a unique combination or SNP haplotypes of the present invention.

Haplotypes are particularly useful in that, for example, fewer SNPs can be genotyped to determine if a particular genomic region harbors a locus that influences a particular phenotype, such as in linkage disequilibrium-based SNP association analysis. Linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium." In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD.

For diagnostic applications, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., obesity, type 2 diabetes) that is influenced by the causative SNP(s). Thus, polymorphic markers that are in LD with causative polymorphisms are useful as diagnostic markers, and are particularly useful when the actual causative polymorphism(s) is/are unknown.

Practitioners skilled in the treatment or diagnosis of metabolic disorders will understand that the information derived from using the methods of the invention is extremely valuable as it can be used to, for example, initiate preventive treatments or to allow an individual carrying one or more significant SNPs or SNP haplotypes to foresee warning signs such as minor clinical symptoms, or to have regularly scheduled physical exams to monitor for appearance of a condition in order to identify and begin treatment of the condition at an early stage (e.g., children).

The present invention also provides methods for assessing the potential response of a subject harboring particular SNP alleles or haplotypes to a particular therapeutic agent or pharmaceutical compound, or to a class of such compounds.

Pharmacogenomics deals with the roles which clinically significant hereditary variations (e.g., SNPs) play in the response to drugs due to altered drug disposition and/or abnormal action in affected persons. The clinical outcomes of these variations can result in severe toxicity of therapeutic drugs in certain individuals or therapeutic failure of drugs in certain individuals as a result of individual variation in metabolism. Thus, the SNP genotype of an individual can determine the way a therapeutic compound acts on the body or the way the body metabolizes the compound. For example, SNPs in drug metabolizing enzymes can affect the activity of these enzymes, which in turn can affect both the intensity and duration of drug action, as well as drug metabolism and clearance.

The SNPs of the present invention also can be used to identify novel therapeutic targets for metabolic disorder. For example, genes containing the disorder associated variants or their products, as well as genes or their products that are directly or indirectly regulated by or interacting with these variant genes or their products, can be targeted for the development of therapeutics that, for example, treat the disorder or prevent or delay disease onset. The therapeutics may be composed of, for example, small molecules, proteins, protein fragments or peptides, antibodies, nucleic acids, or their derivatives or mimetics which modulate the functions or levels of the target genes or gene products.

The SNP-containing nucleic acid molecules disclosed herein, and their complementary nucleic acid molecules, may be used as antisense constructs to control gene expression in cells, tissues, and organisms. The SNPs of the present invention are particularly useful for designing antisense reagents that are specific for particular nucleic acid variants. Based on the SNP information disclosed herein, antisense oligonucleotides can be produced that specifically target mRNA molecules that contain one or more particular SNP nucleotides. In this manner, expression of mRNA molecules that contain one or more undesired polymorphisms (e.g., SNP nucleotides that lead to a defective protein such as an amino acid substitution in a catalytic domain) can be inhibited or completely blocked. Thus, antisense oligonucleotides can be used to specifically bind a particular polymorphic form (e.g., a SNP allele that encodes a defective protein), thereby inhibiting translation of this form, but which do not bind an alternative polymorphic form (e.g., an alternative SNP nucleotide that encodes a protein having normal function).

The SNPs of the present invention are also useful for designing RNA interference reagents that specifically target nucleic acid molecules having particular SNP variants. RNA interference (RNAi), also referred to as gene silencing, is based on using double-stranded RNA (dsRNA) molecules to turn genes off. As with antisense reagents, RNAi reagents may be directly useful as therapeutic agents (e.g., for turning off defective, disease-causing genes), and are also useful for characterizing and validating gene function (e.g., in gene knock-out or knock-down experiments).

The invention further provides a method for identifying a compound or agent that can be used to treat a metabolic disorder. The SNPs disclosed herein are useful as targets for the identification and/or development of therapeutic agents. A method for identifying a therapeutic agent or compound typically includes assaying the ability of the agent or compound to modulate the activity and/or expression of a SNP-containing nucleic acid or the encoded product and thus identifying an agent or a compound that can be used to treat a disorder characterized by undesired activity or expression of the SNP-containing nucleic acid or the encoded product. The assays can be performed in cell-based and cell-free systems. Cell-based assays can include cells naturally expressing the nucleic acid molecules of interest or recombinant cells genetically engineered to express certain nucleic acid molecules.

Variant gene expression in a metabolic disorder patient can include, for example, either expression of a SNP-containing nucleic acid sequence (for instance, a gene that contains a SNP can be transcribed into an mRNA transcript molecule containing the SNP, which can in turn be translated into a variant protein) or altered expression of a normal/wild-type nucleic acid sequence due to one or more SNPs (for instance, a regulatory/control region can contain a SNP that affects the level or pattern of expression of a normal transcript).

EXAMPLES

The following examples illustrate practice of the invention. These examples are for illustrative purposes only and are not intended in any way to limit the scope of the invention claimed.

Example 1

Identification of SNPs in the NPY Pathway Associated with Metabolic Disorder

This example demonstrates the association between the five SNPs (SEQ ID Nos. 1-5) and obesity. The five identified SNPs, rs2342676 (SEQ ID No. 1), hCV44828 (SEQ ID No. 2), hCV44829 (SEQ ID No. 3), hCV1526995 (SEQ ID No. 4), and hCV44837 (SEQ ID No. 5), correlate obesity to a haplotype having at least one copy of chromosome 4 comprising G at position 156702331, A at 156702960, G at 156703137, A at 156706216, and G at 156706781, respectively. In addition, statistically significant association between seven SNPs (SEQ ID Nos. 1-5, 7-8) and risk of developing or protection from obesity and/or risk of developing or protection from type 2 diabetes is shown. An outline of the experimental design is contained in FIG. 1.

The NPY pathway was identified as being of great interest because of compelling pharmacologic data from the human literature, confirmatory mouse genetic data, and the location of several of the genes in this pathway in regions of linkage to obesity.

Genes encoding three related peptides (NPY, PYY, and PPY) as well as their receptors (NPY1R, NPY2R, and NPY5R) were studied for association with obesity and diabetes. These peptides regulate appetite and food intake, and some of the corresponding genes are in regions that have been linked to obesity. Patterns of common variation in these genes were linked in a sample of 96 chromosomes from 12 multi-generational pedigrees of European origin (CEPH).

Figure 2:
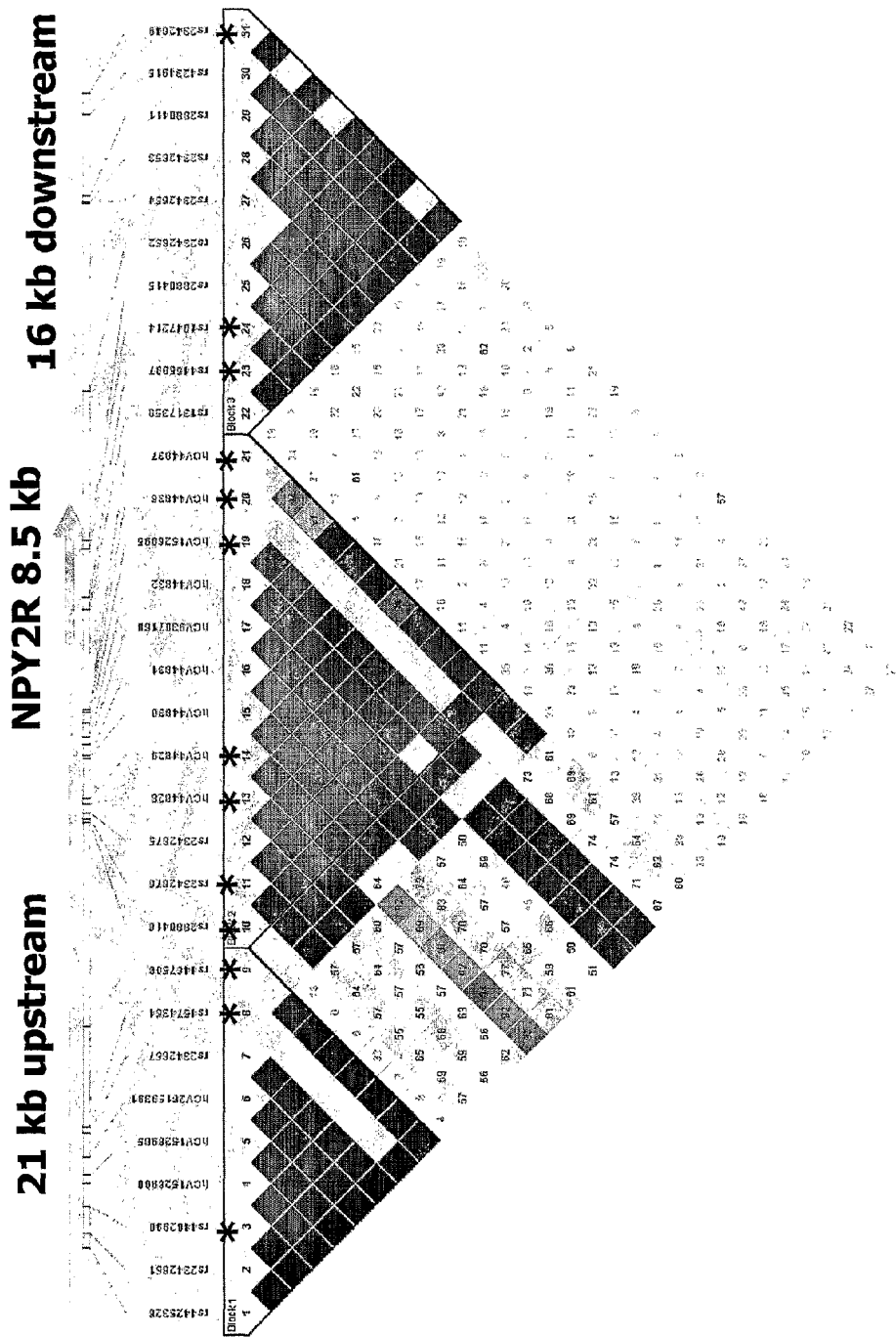
FIG. 2 is a Haploview output showing linkage disequilibrium (LD) patterns at the NPY2R gene.

Single nucleotide polymorphisms (SNPs) were selected from the public database dbSNP, which now contains over 9 million polymorphisms (of an estimated 10 million). These are being typed in the same European-American samples being used to generate the human haplotype map so as to be able to take advantage of rapidly accumulating data from the HapMap efforts. The Haploview software (see FIG. 2) to identify blocks of strong correlation between neighboring markers, and within these blocks, select SNPs that can serve as proxies for the remaining common variation (tag SNPs). FIG. 2 is a Haploview output showing linkage disequilibrium (LD) patterns at the NPY2R gene. Pairwise relationships between each pair of SNPs is shown; strong LD is indicated by solid gray; predominantly gray triangles (outlined in black lines) indicate runs of SNPs that fall within blocks of LD. Within each block, tag SNPs (indicated by *) can be selected that capture the remaining common variation within the block.

Figure 3:
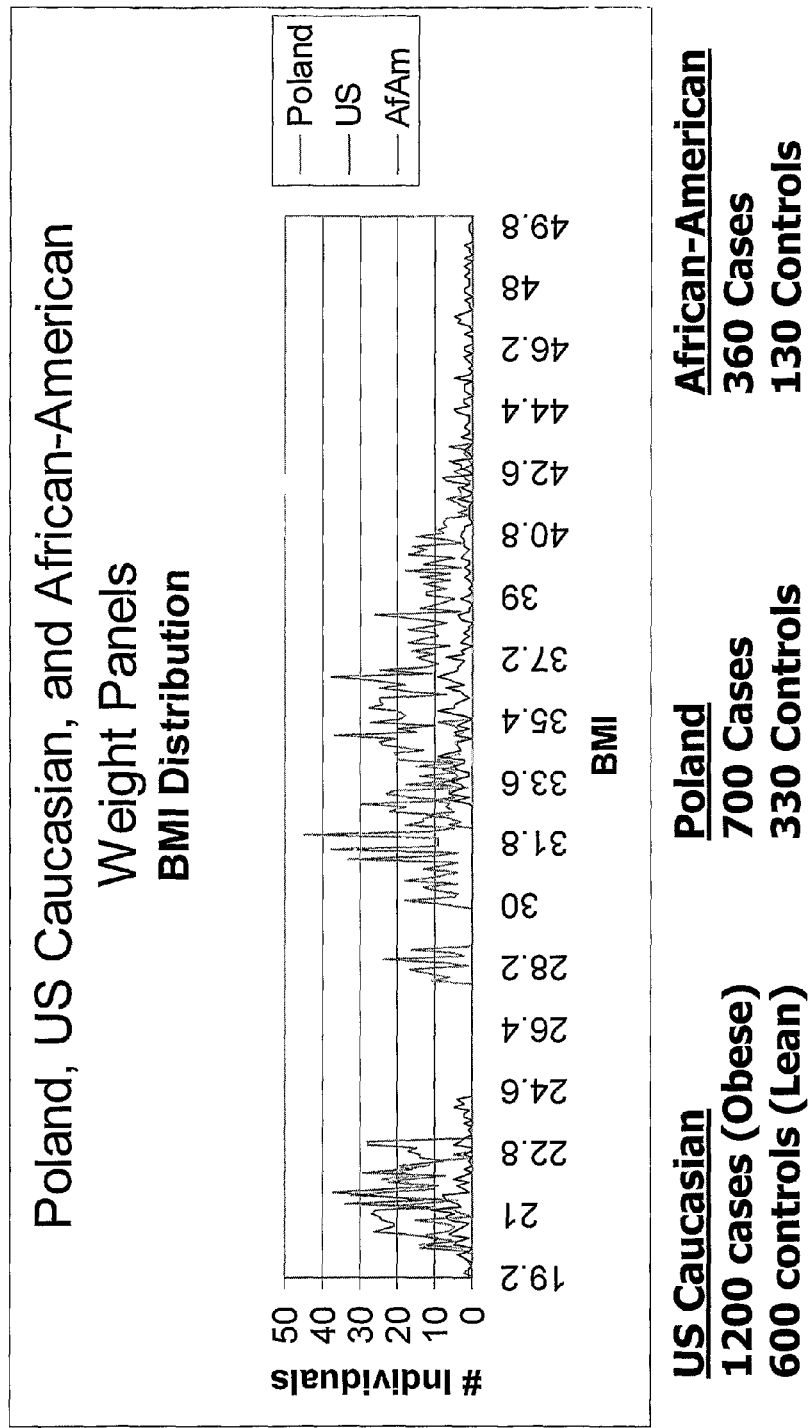
FIG. 3 is a graph of body mass index (BMI) of three populations: a US Caucasian panel, a Polish panel, and an African-American panel.
Figure 5:
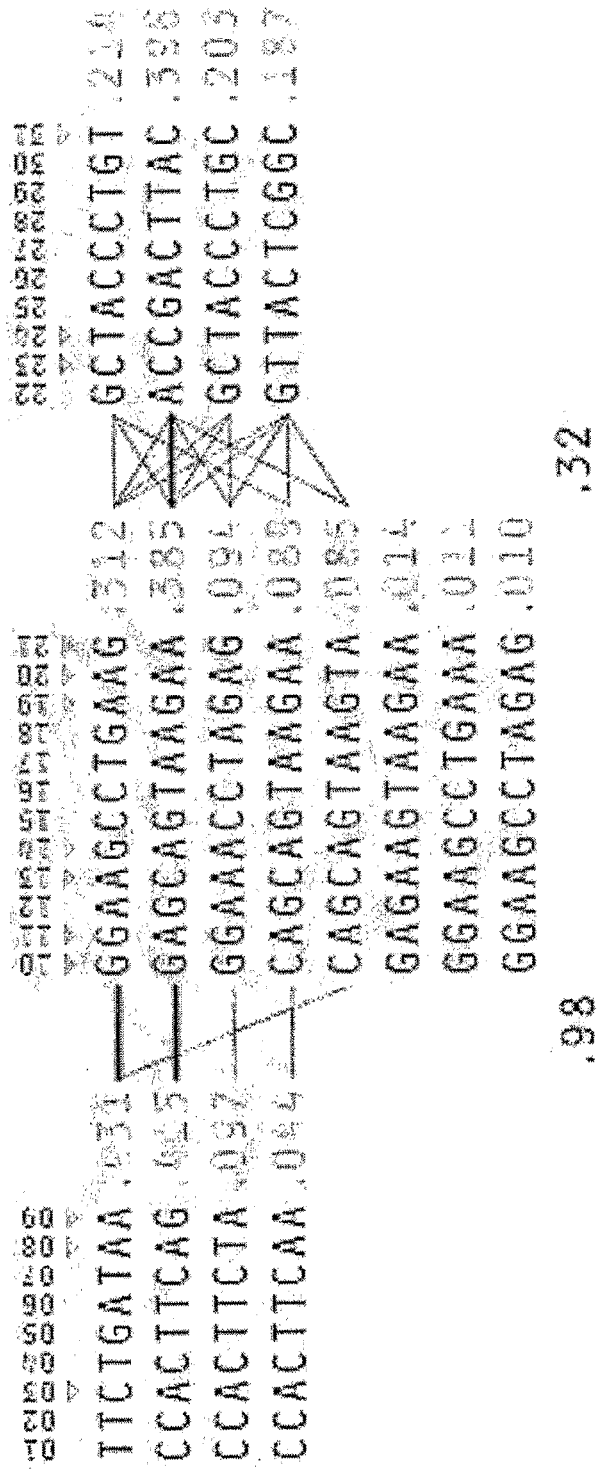
FIG. 5 is a chromosome map showing several NPY2R haplotypes upstream of the NPY2R gene.
Figure 7:
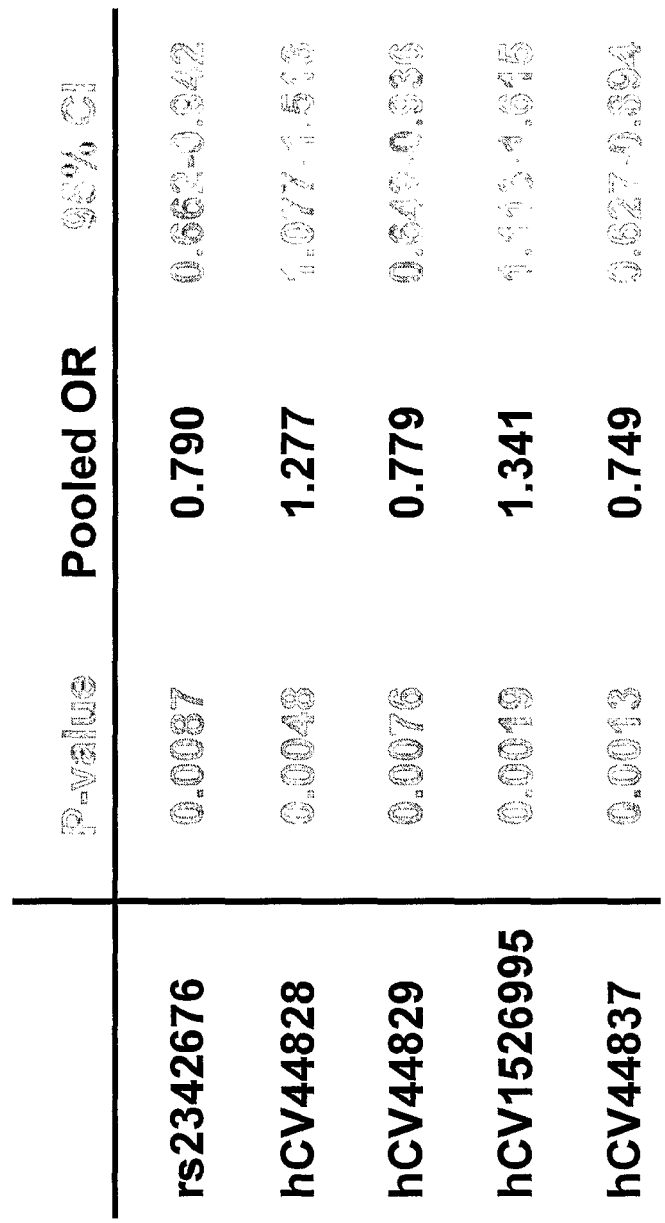
FIG. 7 is a chart of combined statistical data from U.S. and Polish male populations.
Figure 8:
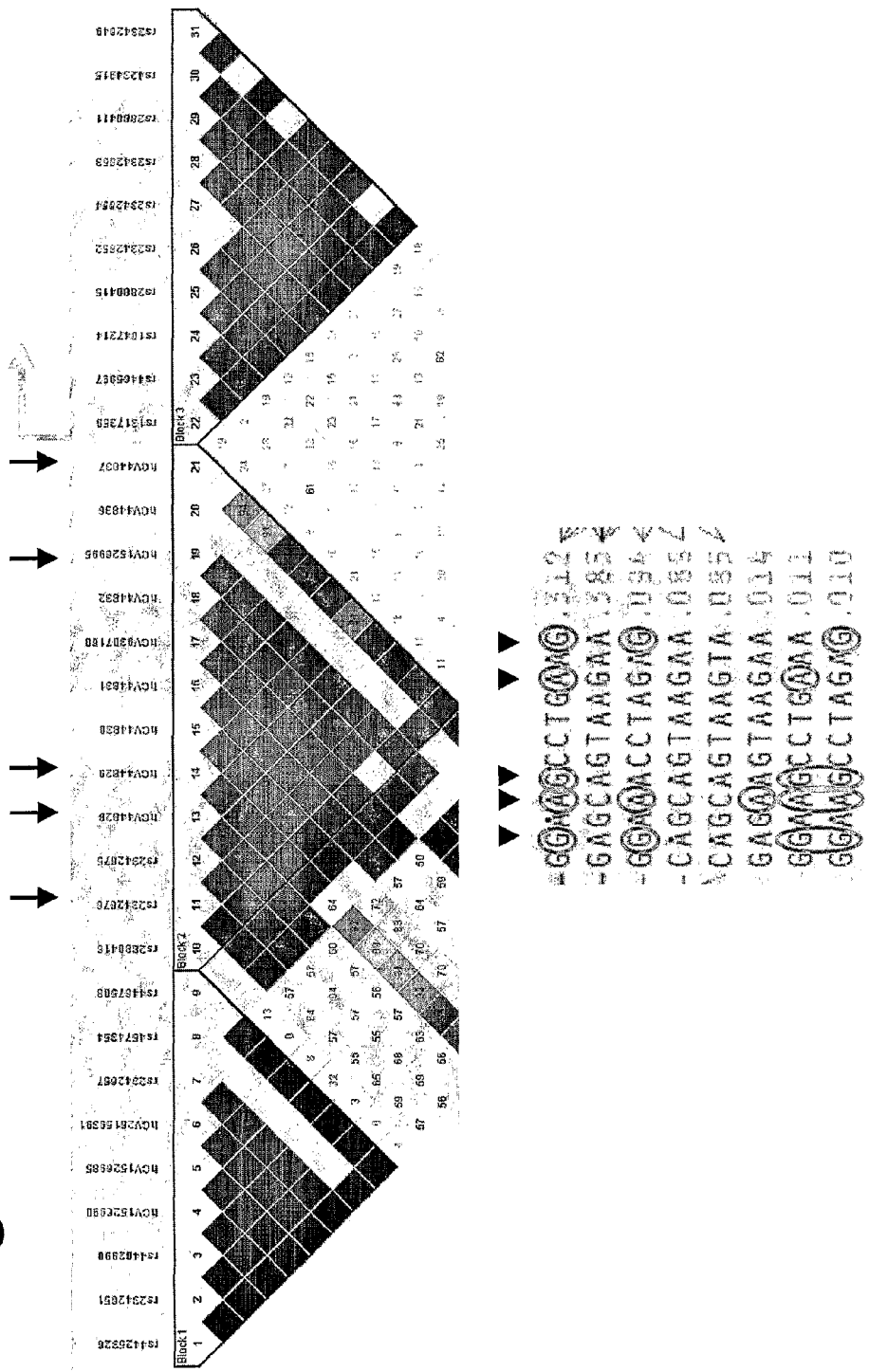
FIG. 8 is a chromosome map showing significant SNPs in NPY2R in men.

Haplotype-tagging SNPs (htSNPs) were selected that capture most of the common variation, and these SNPs were genotyped in patient populations. Two large case-control studies were used, as shown in FIG. 3, a US Caucasian panel and a Polish panel, consisting of cases (1200 US, 700 Poland) from the $90^{th}$-$97^{th}$ percentile in BMI and controls (600 US, 330 Poland) from the $5^{th}$-$12^{th}$ percentile in BMI. In addition, the results were verified using European derived panels consisting of European American, Polish, Framingham, Scandinavian Unrelated and Scandinavian trios. The population of subjects in these groups are outlined in Table 1.

TABLE 1

European-derived panels.

| | European American[a] | | | | Polish[a] | | | | Framingham[b] | | Scandinavian Unrelated[b] | | Scandinavian Trios[c] | |
|---|---|---|---|---|---|---|---|---|---|---|---|---|---|---|
| | Male | | Female | | Male | | Female | | Male | | Male | | Male | |
| | Lean | Obese | Lean | Obese | Lean | Obese | Lean | Obese | Lean | Obese | Lean | Obese | Lean | Obese |
| People | 288 | 552 | 336 | 666 | 151 | 334 | 180 | 366 | 205 | 205 | 240 | 247 | 109 | 109 |
| Age | 56 | 57 | 57 | 58 | 56 | 54 | 57 | 57 | 60 | 60 | 63 | 64 | 30 | 34 |
| +/-s.d. | +/-10 | +/-9 | +/-9 | +/-9 | +/-10 | +/-9 | +/-9 | +/-8 | +/-9 | +/-8 | +/-11 | +/-11 | +/-9 | +/-8 |
| BMI | 22.3+/- | 35.8 | 20.8 | 37.8 | 21.9 | 30.4 | 21.2 | 33 | 23.8 | 34.4 | 22.9 | 30.9 | 22.1 | 28.8 |
| +/-s.d. | 0.5 | +/-2.2 | +/-0.5 | +/-2.3 | +/-0.4 | +/-1.6 | +/-0.8 | +/-1.1 | +/-1.7 | +/-3.3 | +/-1.6 | +/-2.2 | +/-1.9 | +/-3.8 |

[a]Lean subjects are in the $5^{th}$-$12^{th}$ percentile in BMI and Obese subjects in the $90^{th}$-$97^{th}$ percentile in BMI
[b]Lean subjects are in the bottom quartile and obese subjects are in the top quartile of BMI
[c]Lean subjects are below median and obese subject are above median in BMI.

As shown in FIGS. 4-9, an association was observed between several SNPs in NPY2R, encoding the NPY receptor type 2, and obesity in men. Seven SNPs 0.6-5.0 kb upstream of the NPY2R gene showed a significant association with obesity in men in both samples (combined p=0.001, odds ratio=1.34, 95% confidence interval, 1.12-1.59) for the best SNP). For example, the SNP hCV1526995 is associated with obesity in both Poland and US populations (combined p value 0.002, odds ratio 1.34), and this association has been replicated in an independent Scandinavian population (p=0.05, odds ratio=1.19). The association is seen in both US Caucasian and Polish men as shown in FIGS. 6, 7, 9, and 11. The association between metabolic disorders (i.e., obesity and type 2 diabetes) and the seven individual SNPs, the five site haplotype (GAGAG), and the seven site haplotype (GGAGAAG) on chromosome 4 was replicated in a Scandinavian trios study that included 218 men (p=0.019, odds ratio=1.35, 95% confidence interval, 1.02-1.79), a Framingham Heart study sample that included of 410 unrelated men (p=0.223, odds ratio=1.12), and a study of 487 unrelated Scandinavian men (p=0.219, odds ratio=1.12, 95% confidence interval, 0.83-1.51). The five and seven site haplotypes were assigned from either five or seven SNPs in NPY2R, encoding the NPY receptor type 2. A summary of the data from the five male population groups analyzed is shown below in Table 2. No statistically significant (p<0.05) results were found for NPY, PYY, PPY, NPY1R, or NPY5R in the combined panels as shown in FIG. 4.

TABLE 2

Summary of data showing increased risk of obesity in men with the seven site haplotype (GGAGAAG) on chromosome 4.

| Group | n (men) | p-value | Odds ratio (OR) | 95% Confidence Interval |
|---|---|---|---|---|
| European-American | 840 | 0.013 | 1.34 | 1.07-1.71 |
| Polish | 485 | 0.042 | 1.36 | 1.01-1.84 |
| Framingham | 410 | 0.228 | 1.12 | 0.83-1.53 |
| Unrelated Scandinavian | 487 | 0.219 | 1.12 | 1.02-1.79 |
| Scandinavian Trios | 218 | 0.019 | 1.35 | 0.83-1.51 |
| Combined | 2440 | $1.86 \times 10^{-4}$ | 1.27 | 1.12-1.44 |

The sequences of these seven SNPs are given in the Sequence Listing as SEQ ID Nos. 1-5, and 7-8. The seven identified SNPs, rs2880416 (SEQ ID No. 7), rs2342676 (SEQ ID No. 1), hCV44828 (SEQ ID No. 2), hCV44829 (SEQ ID No. 3), hCV1526995 (SEQ ID No. 4), hCV44836 (SEQ ID No. 8) and hCV44837 (SEQ ID No. 5), correlate obesity to G at position 156702170, G at position 156702331, A at 156702960, G at 156703137, A at 156706216, A at 156706671, and G at 156706781, on chromosome 4, respectively. Each SNP alone is useful as a marker as shown in the figures. In addition, the haplotype defined by the GGAGAAG combination bears a strong predictive value for obesity risk. Specifically, at least one copy of a chromosome 4 comprising a G at position 156702170, G at position 156702331, A at position 156702960, G at position 156703137, A at position 156706216, A at position 156706671, and G at position 156706781 on chromosome 4, or those in linkage disequilibrium therewith, indicates that the subject has an increased risk of obesity. The results were replicated (one-tailed p=0.019, odds ratio=1.35) in men from 240 Scandinavian parent-offspring trios. The combined p-value for all three European-derived panels is $1.86 \times 10^{-4}$ (odds ratio=1.27 95% CI, 1.12-1.45). The seven site haplotype GGAGAAG was seen with 31% frequency in a reference sample of European-Americans from the CEPH collection. The SNPs were not significantly associated with obesity in women. The seven site haplotype GGAGAAG also showed only a slight increase in risk of type 2 diabetes (p-value=0.187, OR=1.1, 95% CI=0.95-1.27). These results suggest that common variation in the NPY2R gene influences the development of obesity in men. Because of strong LD in the identified region, there are likely other SNPs that will show the same or potentially even stronger association with obesity.

Further analysis of the seven SNPs led to the discovery that having at least one copy of a chromosome 4 comprising a G at position 156702170, A at position 156702331, C at position 156702960, A at position 156703137, G at position 156706216, A at position 156706671, and A at position 156706781 on chromosome 4, or those in linkage disequilibrium therewith, indicates that the subject has reduced risk of developing the metabolic disorder. The GACAGAA haplotype was found with 39% frequency in a reference sample of European-Americans. This haplotype was found to be significantly statistically associated with protection from developing both obesity (p=0.006, odds ratio=0.85, 95% confidence interval=0.75-0.95) and type 2 diabetes (p=$6.53 \times 10^{-4}$, odds ratio=0.78, 95% confidence interval=0.67-0.90).

In addition, the seven site haplotype on chromosome 4 comprising CACAGAA was found to be statistically significantly associated with an increased risk of type 2 diabetes. Specifically, the genetic variation comprising at least one copy of a chromosome 4 comprising a C at position 156702170, A at position 156702331, C at position 156702960, A at position 156703137, G at position 156706216, A at position 156706671, and A at position 156706781 on chromosome 4, or those in linkage disequilibrium therewith, was shown to significantly increased risk of diabetes. The CACAGAA haplotype was found with 9% frequency in a reference sample of European-Americans. This haplotype was found to be significantly statistically associated with increased risk of developing type 2 diabetes (p=$4.02 \times 10^{-6}$, odds ratio=1.75, 95% confidence interval=1.38-2.22). The haplotype was associated with a decreased risk of obesity (p=0.223, odds ratio=0.89, 95% confidence interval=0.73-1.08).

Figure 13:
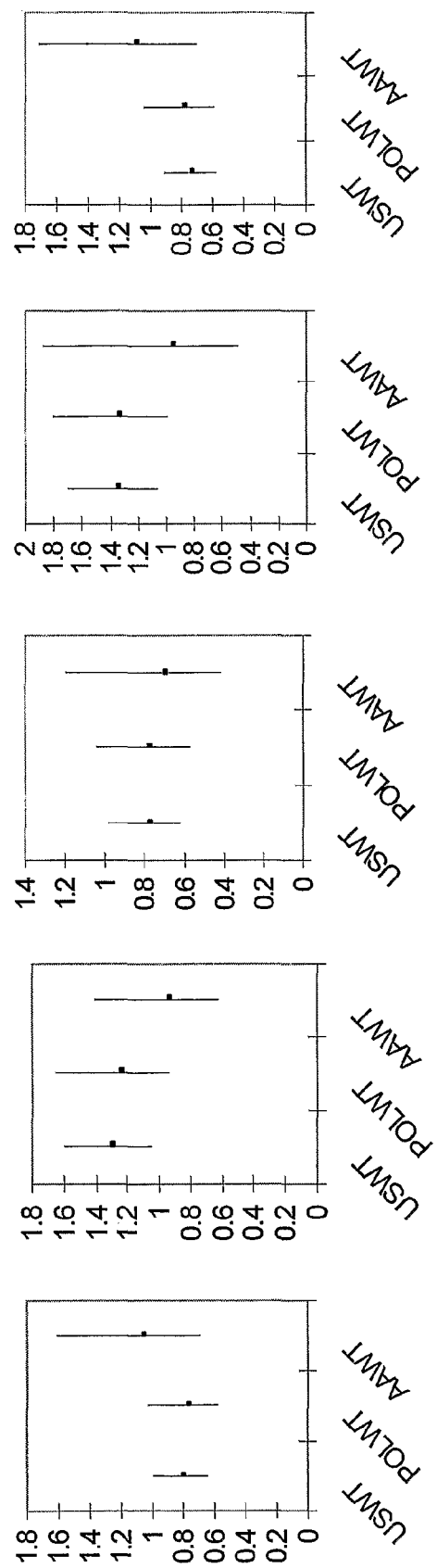
FIG. 13 shows five graphs of confidence intervals from the African American population group.

Standard chi-square analysis was used for case control studies and the transmission disequilibrium test (TDT) for family-based samples (Spielman R S, Ewens W J (1996) The TDT and other family-based tests for linkage disequilibrium and association. *Am J Hum Genet.* 59(5):983-989). For the GCI case control samples, lean and obese individuals were selected to be in the 5th-12th percentile and the 90th-97th percentiles for their age and decade and life, based on distributions of healthy controls from the same populations. Three populations were studied, US Caucasians, Poland, and African-American. For the Scandinavian replication samples (looking for effects in males only), the fathers from the related sample were combined with other unrelated men who are controls (unaffected) from samples used to study type 2 diabetes to create a case control study (obese=top quartile, lean=bottom quartile) and by a TDT analysis (obese male offspring=above median, lean male offspring=below median). A case-control analysis was also performed on the men from the Framingham Heart Study (obese=top quartile, lean=bottom quartile). Statistical evidence was combined as described in Lohmueller (Lohmueller K E, Pearce C L, Pike M, Lander E S, Hirschhorn J N. Meta-analysis of genetic association studies supports a contribution of common variants to susceptibility to common disease. *Nat Genet* 2003;33: 177-82). The odds ratio (OR), a way of comparing whether the probability of a certain event is the same for two groups wherein OR greater than one implies that the event is more likely in the first group, was calculated for each group. The results from the African American men were not significant since there was not enough power. As shown in FIGS. 12 and 13, when African American Weight (AAWT) was evaluated, the P-values were not significant and the odds ratios were not consistent.

An assessment of stratification in the populations has been completed. The Poland population had no evidence of stratification, and the US population had only mild evidence of stratification that can be easily corrected for. Thus, the associations observed in the US and Poland populations will not be false positives due to stratification. These results suggest that common variation in the NPY2R gene influences the development of obesity in men. Hence, NPY2R is an excellent target for development of pharmaceuticals and small molecules that block or enhance NPY2R function. Since NPY2R is a receptor with known ligands (NPY, PYY and PPY), this could facilitate drug development.

Example 2

Identification of SNPs Associated with Metabolic Disorders

More than 15 additional high quality candidate genes have been identified. These candidate genes were derived from cross-referencing *C. elegans* RNAi screening results with human genetic linkage data, and then choosing genes in both datasets that are also relevant to the mitochondrial pathway. A complete list of genome-wide linkage studies of obesity and body mass index was assembled from the literature From this literature, regions of the genome that show evidence of linkage to obesity were identified. Genome scan meta-analysis (GSMA) were then performed to rank these regions in order of priority.

These human genomic regions with the likely human orthologs for the set of *C. elegans* genes identified in the RNAi screen for fat storage were cross referenced. This process identified three genes that affected fat storage in *C. elegans*, are in regions of linkage to obesity in humans, and also directly related to mitochondrial energy metabolism. PCK1 encodes phosphoenolpyruvate carboxykinase, a key regulatory step in mitochondrial energy metabolism that is part of the mitochondrial oxidative phosphorylation (OXPHOS) pathway. TPRT encodes trans-prenyltransferase, a protein involved in coenzyme Q metabolism; coenzyme Q is a key cofactor in OXPHOS. ACAS2 encodes acetyl-coA synthetase, a mitochondrial enzyme involved in fat metabolism. A fourth gene that was identified by both *C. elegans* and human studies, DRD2 (encoding the D2 dopamine receptor), was studied for a role in human obesity.

Key regulators were chosen from the OXPHOS pathway, preferentially selecting genes located in regions of linkage to BMI or those identified in the *C. elegans* screens. In addition, the BBS genes responsible for Bardet-Biedl syndrome, a single-gene disorder that causes obesity in humans, were chosen because these genes were also identified in unpublished *C. elegans* work. Finally two genes other genes that lie in regions of linkage to BMI were chosen: TUB (encoding the tubby homologue) and TPH1 (encoding tryptophan hydroxylase). Once the patterns of common variation is defined, haplotype-tagging SNPs (htSNPs) that capture most of the common variation htSNPs in patient populations will be genotyped, and single SNPs and haplotypes will be tested for association.

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

The invention claimed is:

1. A method of determining the risk of developing, or determining whether a male human subject has or is predisposed to developing type 2 diabetes comprising:
   a) detecting the presence of at least one genetic variation in a nucleic acid sample from the male human subject wherein the at least one genetic variation comprises a NPY2R-associated single nucleotide polymorphism of a C at position 156702170 on chromosome 4, and
   b) identifying the male human as having or predisposed to developing type 2 diabetes.

2. The method of claim 1, wherein the step of detecting the presence of at least one genetic variation of further comprises detecting at least one additonal single nucleotide polymorphism on at least one copy of a chromosome 4, the additional polymorphism is selected from the group consisting of A at position 156702331, C at position 156702960, A at position 156703137, G at position 156706216, A at position 156706671, and an A at position 156706781 on chromosome 4.

3. The method of claim 1, wherein said detecting step is selected from the group consisting of size analysis; sequencing; hybridization; 5' nuclease digestion; single-stranded conformation polymorphism; allele specific hybridization; primer specific extension; and oligonucleotide ligation assay.

4. The method of claim 1, wherein prior to or in conjunction with detection, the nucleic acid sample is subject to an amplification step.

5. A method of claim 3, wherein said size analysis is preceded by a restriction enzyme digestion.

6. The method of claim 1, wherein the sample is selected from the group consisting of blood, saliva, amniotic fluid, and tissue.

7. The method of claim 1, wherein said detecting step is selected from the group consisting of a nucleic acid sequence scanning assay and a specific mutation detection assay.

8. The method of claim 1, wherein said nucleic acid is selected from the group consisting of mRNA, genomic DNA, and cDNA.

9. A method of screening for predisposition to type 2 diabetes in a male human subject comprising:
   a) detecting the presence of a NPY2R-associated single nucleotide polymorphism on at least one copy of chromosome 4 comprising C at position 156702170,
   b) detecting the presence of at least one additional single nucleotide polymorphism on at least one copy of chromosome 4 comprising at least one of the group consisting of A at position 156706671, A at position 156702331, C at position 156702960, A at position 156703137, G at position 156706216, and A at position 156706781, and
   c) identifying the male human as having or predisposed to developing type 2 diabetes.

* * * * *